United States Patent [19]

Damiano

[11] 3,991,116

[45] Nov. 9, 1976

[54] 4-TERT-BUTYL-N-SEC-BUTYL-2,6-DINITROANILINE

[75] Inventor: John Joseph Damiano, Springfield, Pa.

[73] Assignee: Amchem Products, Inc., Ambler, Pa.

[22] Filed: May 1, 1975

[21] Appl. No.: 573,634

Related U.S. Application Data

[60] Continuation-in-part of Ser. Nos. 263,511, June 16, 1972, abandoned, and Ser. No. 266,035, June 26, 1972, abandoned, said Ser. No. 263,511, is a division of Ser. No. 89,010, Nov. 12, 1970, Pat. No. 3,672,866, which is a continuation-in-part of Ser. No. 878,583, Nov. 20, 1969, abandoned, said Ser. No. 266,035, is a continuation-in-part of Ser. No. 89,010.

[52] U.S. Cl. .................................. 260/577; 71/121; 260/646

[51] Int. Cl.$^2$ ..................... C07C 87/50; A01N 9/20
[58] Field of Search ...................... 200/577; 71/121

[56] References Cited
UNITED STATES PATENTS

| | | | |
|---|---|---|---|
| 3,111,403 | 11/1963 | Soper | 260/577 X |
| 3,332,769 | 7/1967 | Soper | 260/577 X |

*Primary Examiner*—Daniel E. Wyman
*Assistant Examiner*—John J. Doll
*Attorney, Agent, or Firm*—Ernest G. Szoke; Michael E. Zall

[57] ABSTRACT

The novel 4-tert-butyl-N-sec-butyl-2,6-dinitroaniline and its optically active enantiomorphs are useful as herbicides, piscicides, for aquatic weed control and for dodder control.

3 Claims, No Drawings

4-TERT-BUTYL-N-SEC-BUTYL-2,6-DINITROANILINE

This application is a continuation-in-part of application Ser. No. 263,511, filed June 16, 1972, now abandoned and Ser. No. 266,035, filed June 26, 1972, now abandoned.

Application Ser. No. 263,511 is a division of application Ser. No. 89,010, filed Nov. 12, 1970 now U.S. Pat. No. 3,672,866, which, in turn, is a continuation-in-part of application Ser. No. 878,583 filed Nov. 20, 1969, now abandoned.

Application Ser. No. 266,035 is a continuation-in-part application of application Ser. No. 89,010 filed Nov. 12, 1970, now U.S. Pat. No. 3,672,866, which, in turn, is a continuation-in-part of application Ser. No. 878,583 filed Nov. 20, 1969, now abandoned.

The entire disclosures of these earlier filed applications are incorporated herein by reference.

This invention relates to novel mono-N-substituted derivatives of 4-(sec-butyl)-2,6-dinitroaniline and 4-(t-butyl)-2,6-dinitroaniline and their optically active enantiomorphs, and to novel formulations containing these compounds as the major active ingredient.

Certain known 2,6-dinitroaniline derivatives have obtained importance in recent years inasmuch as they have been found to have high herbicidal activity and thus to serve well for the elimination of grasses and broadleaf plants infesting drainage ditches, gravel walks, road shoulders or wooded areas. The dinitroaniline derivatives are also suitable as herbicides between rows of crops in corn, cotton or soybean fields, strawberry patches and similar crop-bearing areas, provided these herbicides are applied in such a way that they do not harm the crop-bearing plants. Still another advantageous use of the herbicidal properties of these dinitroaniline derivatives is to employ them as preemergence herbicides at the time of planting of such crop plants as corn, cotton, soybeans, wheat, sugar beets, and the like. When thus applied, the dinitroaniline derivatives will eliminate the germinating weeds without adversely affecting the germination and growth of the desired crop plants.

Among the dinitroaniline derivatives which have found commercial acceptance a,a,a-trifluoro-2,6-dinitro-N-N-dipropyl-p-toluidine, also known as trifluralin and 4-(methylsulfonyl)-2,6-dinitro-N-N-dipropylaniline, also known as nitralin, are being used as preemergence herbicides on cotton, soybeans, dry beans, sugar beets, peas and other crops. Other specific dinitroaniline derivatives which have been suggested for controlling weeds in crop areas include 2,6-dinitroaniline itself and its N-ethyl and N-n-propyl derivatives, 2,6-dinitro-p-toluidine and its N,N-di-n-propyl and -diallyl derivatives. Compounds of this type are disclosed, for example, in U.S. Pat. Nos. 3,111,403; 3,257,190; 3,332,769; 3,403,180 and 3,449,111 and German patent publication DAS No. 1,300,727.

In spite of the good herbicidal activity of these dinitroaniline derivatives, none of them is entirely satisfactory in every respect. Some of them are too costly to allow wide-spread and general application since they are only available through complicated synthesis techniques which involve several steps that give relative low yields. The preparation of still other derivatives involve unstable nitro-derivatives, the handling of which is hazardous and dangerous. Some of the dinitroaniline derivatives recommended as herbicides are not sufficiently selective in their activity and too often they also affect adversely the crop plants, even if care has been taken to use the chemicals at their lowest effective level and to avoid direct contact with the crop plants. Further, some of the dinitroanilies do not have activity, or sufficient activity for a desirable use, herbicidal or otherwise.

Generally speaking, those dinitroaniline derivatives which have proven to be commercially acceptable are the N,N-disubstituted derivatives and particularly those having a functional group other than alkyl, for example, halo, haloalkyl, methylsulfonyl and the like, para to the amino group. Among the N,N-disubstituted compounds of the prior art having an alkyl substituent para to the amino group, the methyl derivative has been generally found to be more effective than the higher alkyls, e.g. propyl or butyl. Accordingly, prior investigators have turned to dinitro derivatives having, as noted above, functional groups other than alkyl in para position or no functional group and where alkyl derivatives have been explored, experience has favored the shortest carbon chain derivatives. Similarly, in the case of the substituents on the nitrogen atom, the di-substituted derivatives have been favored over mono-substituted derivatives.

In accordance with this invention, it has been found that notwithstanding the experience with N,N-disubstituted derivatives wherein an increase in the size of the alkyl substituent in para position diminishes herbicidal effectiveness, there can be obtained "herbicidally active" compounds of unusually high activity and particularly good selectivity in a variety of agronomic crops when a branched chain butyl substituent, particularly the tert-butyl, is introduced in para position of 2,6-dinitroaniline with n-mono-alkyl substitution. The N-monoalkyl derivatives especially the N-propyl and N-butyl derivatives, and particularly the isopropyl, sec-butyl and tert-butyl derivatives have proven to be unusually effective herbicides with respect to both weed control and crop safety, growth and yield. The herbicidal effectiveness of the N-mono substituted compounds of this invention is particularly surprising when compared to the effectiveness of the corresponding N,N-disubstituted derivatives. For example, the 4-tert-butyl-N-sec-butyl-2,6-dinitroaniline of this invention has been shown to possess unique selective herbicidal properties, whereas the corresponding 4-tert-butyl-N,N-di-sec-butyl-2,6-dinitroaniline is lacking any practical herbicidal activity.

More importantly, it has been discovered that the novel derivatives of this invention have desirable plant regulant properties, notably increased plant vigor resulting in improved yields and other plant regulant effects, such as tobacco sucker control. The surprising ability of the novel compounds of this invention to suppress the occurrence of "suckers" or lateral buds on tobacco plants which have been recently topped to remove the flowering portion of the plant presents an unusual economic benefit by extending the utility of the compounds significantly beyond the known applications for the related prior art dinitroanilines. This ability to suppress tobacco suckering is a well recognized growth regulant activity, not expected of a herbicidally active compound.

Further, the novel derivatives of this invention exhibit new and useful properties not exhibited by the closest prior art compounds.

Accordingly, it is the object of this invention to provide certain new compounds which are among other uses, highly effective as herbicides and which can be readily prepared by a convenient synthetic process and which compounds, when employed as herbicides, have demonstrated minimal or, essentially, no deleterious effect on crop plants.

Another object of this invention is the provision of active dinitroaniline derivatives, the synthesis of which does not require hazardous operations or raw materials or intermediates not readily available.

It is a more specific object of this invention to provide 4-tert-butyl-N-sec-butyl-2,6-dinitroaniline and its optically active isomers, all of which are particularly useful as plant regulants and specifically as tobacco sucker control agents.

Other objects of this invention will be apparent from the description that follows.

The novel compounds of this invention are represented by the general formula:

Bu—⟨benzene ring with NO$_2$ at 2-position, NHR at 1-position, NO$_2$ at 6-position⟩ wherein Bu represents t-butyl or sec-butyl and R represents a branched chain alkyl of 3 to 6 carbon atoms, cyclo-lower-alkyl, cyclo-lower-alkyl-lower-alkyl, lower alkenyl, lower alkynyl, lower alkoxy-lower alkyl or di-lower-alkoxy-lower-alkyl.

Particularly preferred compounds of this invention are when R is a branched chain propyl or butyl.

As used herein the term branched chain alkyl of 3 to 6 carbon atoms denotes branched chain hydrocarbons containing 3 to 6 carbon atoms. The highly preferred compounds are the branched 3 and 4-carbon groups i-propyl, sec-butyl and t-butyl.

The term cycloalkyl denotes monocyclic saturated hydrocarbons having 3 to 6 carbon atoms; such as cyclopropyl, cyclopentyl, cyclohexyl.

The term cyclo-lower-alkyl-lower-alkyl denotes groups such as cyclopropyl methyl, cyclohexylmethyl, etc.

The term lower alkenyl denotes straight or branched chain hydrocarbons having 3 to 4 carbon atoms and at least one double bond such as allyl, 2-butenyl, 3-butenyl, pentenyl, hexenyl and the like.

The term lower alkynyl denotes straight or branched chain hydrocarbons having 3 to 4 carbon atoms and at least one triple bond such as propynyl, 2-butynyl, 3-butynyl, pentynyl and the like.

The term lower-alkoxy-lower-alkyl denotes a $CH_3(CH_2)m — O — (CH_2)n$-group wherein $m$ is 0 or 1 and $n$ is an integer from 1 to 6, such as methoxymethyl, methoxyethyl, methoxypropyl, methoxyisopropyl, ethoxymethyl, ethoxyethyl, ethoxypropyl, ethoxyisopropyl, etc.

The term di-lower alkoxy-lower-alkyl denotes a $(CH_3(CH_2)m-O)_2$ $C_n$ $H_{2n+1}$ - group wherein $m$ and $n$ have the same meaning as above such as dimethoxymethyl, dimethoxyethyl, dimethoxypropyl, dimethoxyisopropyl, diethoxymethyl, diethoxyethyl, diethoxypropyl, diethoxyisopropyl, etc.

A particularly preferred novel compound of this invention is 4-tert-butyl-N-sec-butyl-2,6-dinitroaniline and its optically active dextro and levo rotatory isomers.

The compounds of this invention are synthesized by an especially facile route which takes advantage of the readily accessible dinitrophenol derivatives as the intermediate. The reaction sequence is shown graphically in the following schematic diagram:

Bu—⟨benzene⟩—OH  $\xrightarrow{HNO_3/H_3CCOOH}$  Bu—⟨benzene with NO$_2$, NO$_2$⟩—OH

I.                                             II.

Bu—⟨benzene with NO$_2$, NO$_2$⟩—OH  $\xrightarrow{\text{chlorinating-agent complex}}$  Bu—⟨benzene with NO$_2$, NO$_2$⟩—Cl

II.                                            III.

Bu—⟨benzene with NO$_2$, NO$_2$⟩—Cl  $\xrightarrow{H_2NR}$  Bu—⟨benzene with NO$_2$, NO$_2$⟩—NHR

III.                                           IV.

In the first step of the process a para-t-butylphenyl or a para-sec-butylphenol, both of which are readily available, low cost starting materials, is nitrated by treating the phenol with nitric acid in acetic acid solution to give the corresponding 2,6-dinitrophenol in good yield. The nitration step follows known procedures for nitrating phenols as will be more fully apparent from the specific examples given hereinbelow.

The 2,6-dinitro-4-Bu-phenol obtained as above is then converted to the corresponding chloro compound of Formula III. This transformation which forms a key step in the process for preparing the novel compounds of this invention is accomplished by employing a chlorinating agent such as thionyl chloride, phosphorus oxychloride or phosphorus pentachloride in the presence of a complexing agent as described below. Such chlorination agents are well known in the art, though it has been found that the above described chlorination is not effected, under the usual reaction conditions previously known to the art, wherein the chlorination is accomplished by treating the phenol starting material with a chlorinating agent in an inert solvent.

Thus, for example, Capon and Chapman (J. Chem. Soc. 1957, p. 600) prepared 5-tert-butyl-2,4-dinitrochlorobenzene from para-tert-butyl-aniline by the reaction sequence involving acetylation, chlorination, Sandmeyer's reaction, and nitration.

As another example, the synthesis of 6-tert-butyl-2,4-dinitrochlorobenzene may be mentioned, which was accomplished (C.A. 50, 11260b) by nitrating 2-tert-butylphenol, methylation of the resulting dinitro derivative, conversion of the methoxy compound into the amine, followed by diazotization and Sandmeyer's reaction.

It has now been found that the chlorination of the 2,6-dinitro-4-Bu-phenol can be carried out by employing as the chlorinating agent, a combination of one of the above mentioned chlorinating agents and an amide, such as formamide, acetamide, propionamide, acetamide, propionamide or their alkylated derivatives, e.g. dimethyl formamide (DMF), etc. The chlorinating agent and acetamide are used in about equimolar amounts or, if desired, the chlorinating agent can be used in excess, though the acetamide and chlorinating agent should ordinarily both be present in amounts equal to or greater than the 2,6-dinitro-4-Bu-phenol intermediate on a molar basis. The reaction is conveniently carried out in an inert organic solvent, such as toluene, xylene and the like.

A preferred reaction temperature is the reflux temperature of the reaction mixture (about 110° to 120°C) though higher or lower temperatures can also be employed with correspondingly shorter or longer reaction times.

The reaction is ordinarily completed in about 12 to 16 hours, at which time the excess chlorinating agent can be readily stripped from the desired mixture by evaporating under reduced (about 30mm) pressure. The desired chlorinated compound remains in the supernatant liquid as a heavy liquid and is easily removed from the liquid supernatant.

The product obtained in this way can be precipitated from an inert organic solvent, such as n-hexane, to give pure 2,6-dinitro-4-Bu-chlorobenzene in good yield.

In the final step of the reaction sequence, the chlorinated intermediate of Formula III is converted to the desired end product of Formula IV by treating with the appropriate primary amine. These amines are generally liquid and soluble in the usual inert organic solvents, such as toluene, xylene, alcohol and the like, employed as the reaction medium. Where the amine is water soluble an aqueous medium, such as an alcohol-water solvent can be conveniently employed. The reaction is readily effected by adding, dropwise, a solution of the amine reactant in the appropriate solvent to the chlorinated intermediate, also in the same solvent. The amine is ordinarily employed in an excess amount on a molar basis. Upon completion of the addition, the mixture is refluxed until the reaction is completed.

The course of the reaction can be followed by the formation of the hydrochloride salt of the unreacted amine which usually separates out as a solid precipitate. The precipitate is filtered out and the filtrate evaporated to dryness. The solid residue is recrystallized from an organic solvent, such as methanol, ethanol or the like to give a pure product.

Alternatively the novel compounds of this invention can, if desired, be prepared by treating the 4-butyl-2,6-dinitrophenol intermediate with p-toluene sulfonyl chloride or methyl sulfonyl chloride or similar reagent according to known methods to introduce a tosyl or mesyl or similar leaving group. The corresponding tosylate or similar derivative can be readily aminated by known procedures.

The preparation of the novel compound of this invention will be further understood from the further specific examples which are intended to be illustrative only.

EXAMPLE I

Following the method of Dutton, et al. (Canadian Journal of Chemistry, Vol. 31, p. 685, 1953), 200 grams (1.32 moles) 4-tert-butylphenol was dissolved in 480 ml. glacial acetic acid and added dropwise over a period of one hour to a stirred solution of 320 ml. of 90% nitric acid and 600 ml. of glacial acetic acid at −10° to −15° C. After complete addition the temperature rises to 0 to −5° C. The reaction mixture is then allowed to come to room temperature and maintained there for one hour. The mixture is then poured onto cracked ice, diluted with water and cooled. The product is then filtered, washed with $H_2O$, dried and recrystallized from hot hexane to give 180 grams of 2,6-dinitro-4-tert-butylphenol in the form of fine yellow needles melting at 94° – 95° C.

180 grams (0.75 moles) of 2,6-dinitro-4-tert-butylphenol thus prepared was placed in a mixture of 113 grams (0.95 moles) thionyl chloride, 55 grams (0.76 moles) dimethylformamide and 300 ml. of dry toluene. The mixture was stirred and heated to reflux temperature for 15 hours after which time the thionyl chloride, DMF and toluene were removed under reduced pressure until a slush remained. Hexane was then added to the reaction vessel, the mixture cooled and filtered. The product was then recrystallized from boiling hexane to give 168 grams 2,6-dinitro-4-tert-butylchlorobenzene in the form of light yellow needles melting at 114° – 116° C.

EXAMPLE II 1 gram of 2,6-dinitro-4-tert-butylchlorobenzene was allowed to react with 1 gram of sec-butylamine by adding the amine dropwise to a refluxing mixture of 50 ml. dry toluene, and the 2,6-dinitro-4-tert-butylchlorobenzene. After complete addition, the mixture was refluxed 8 hours, cooled to room temperature, the amine hydrochloride filtered off, and toluene and unreacted amine were removed under reduced pressure. The thick material that resulted was dissolved in hot ethanol and the product was crystallized upon cooling to yield 4-tert-butyl-N-sec-butyl-2,6-dinitroaniline melting at 60°–62° C.

EXAMPLE III 4.5 grams (0.11 moles) of sodium hydroxide was dissolved in 100 ml. of methanol. 32.4 grams (0.10 moles) of 4-tert-butyl-2,6-dinitrophenol was dissolved in the resultant solution. 23 grams (0.12 moles) of tosyl chloride was added and the mixture stirred at 35° C for 1.5 hours. The solid was filtered and washed with water to obtain 33 grams (84% yield) of a light yellow tosylate product melting at 124°–130° C.

29.4 grams (0.10 moles) of tosylate and 14.6 grams (0.20 moles) of sec-butylamine in 200 ml. of water was stirred and heated at reflux for 3 hours. After cooling to room temperature the mixture was filtered and the solid washed with water. The dried product, 4-tert-butyl-N-sec-butyl-2,6-dinitroaniline, weighed 23.6 grams (80% yield).

EXAMPLE IV

Two and six-tenths grams (.01 mole) of 2,6-dinitro-4-t-butylchlorobenzene was reacted with 3.1 grams of 40% aqueous solution of methylamine in 50 ml. ethanol. The temperature was slowly increased as follows: 30° C for 1 hour; 40° C for 1 hour; 50° C for 1 hour, then 80° C for 5 hours. When the reaction was complete about 100 ml. H₂O was added, precipitating the product. This was filtered, washed with portions of H₂O and upon recrystallization from ethanol yielded 2.5 grams of N-methyl-2,6-dinitro-4-t-butylaniline as orange needles melting at 129°–130° C.

EXAMPLE V

By using a method similar to those described in the preceding examples, the following additional 4-t-butyl-2,6-dinitroaniline derivatives were prepared by reacting 4-t-butyl-2,6-dinitrochlorobenzene with the appropriate amine. These compounds, together with those mentioned in the preceding examples, are listed in Table I.

Table I

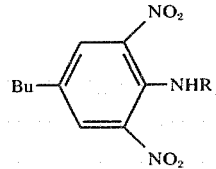

| No. | Amino Reactant | Bu | R | m.p. |
|---|---|---|---|---|
| 1 | methylamine | t-butyl | methyl | 129–130° C. |
| 2 | ethylamine | t-butyl | ethyl | 70–73° C. |
| 3 | i-propylamine | t-butyl | i-propyl | 71–73° C. |
| 4 | n-butylamine | t-butyl | n-butyl | 63–65° C. |
| 5 | sec-butylamine | t-butyl | s-butyl | 60–62° C. |
| 6 | t-butylamine | t-butyl | t-butyl | 81–83° C. |
| 7 | t-pentylamine | t-butyl | t-pentyl | 49–56° C. |
| 8 | isopentylamine | t-butyl | i-pentyl | 38–40.5° C. |
| 9 | allylamine | t-butyl | allyl | 56–58° C. |
| 10 | 3-methoxypropylamine | t-butyl | methoxy propyl | 41–45° C. |
| 11 | 2,2-dimethoxyethylamine | t-butyl | β,β-dimethoxyethyl | Dark organic liquid |
| 12 | cyclohexylamine | t-butyl | cyclohexyl | 89–90° C. |
| 13 | n-hexylamine | t-butyl | n-hexyl | Liquid |
| 14 | cyclopropylamine | t-butyl | cyclopropyl | 125–126.5° C |
| 15 | cyclopropylmethylamine | t-butyl | cyclopropylmethyl | |
| 16 | methylamine | sec-butyl | methyl | Dark organic liquid |
| 17 | ethylamine | sec-butyl | ethyl | 44–45° C. |
| 18 | isopropylamine | sec-butyl | i-propyl | Semi-solid |
| 19 | sec-butylamine | sec-butyl | s-butyl | Dark organic liquid |
| 20 | n-butylamine | sec-butyl | n-butyl | Liquid |
| 21 | t-butylamine | sec-butyl | t-butyl | 33–38° C. |
| 22 | cyclohexylamine | sec-butyl | cyclohexyl | 65–67° C. |
| 23 | 2,2-dimethoxyethylamine | sec-butyl | dimethoxyethyl | Liquid |
| 24 | 3-methoxypropylamine | sec-butyl | 3-methoxypropyl | Liquid |

The optically active isomers are prepared by any of the synthesis routes described above, utilizing the optically active form of sec-butyl-amine (either the d-form or the l-form) in the amination step. The optically active d-sec-butyl amine and l-sec-butyl amine intermediates are readily prepared from racemic sec-butyl amine by methods known, per se. Thus, for example, d-tartaric acid can be reacted with a racemic mixture of sec-butyl amine and the d-sec-butyl amine-d-tartrate separated by fractional precipitation from the reaction mixture as a crystalline precipitate. Alkaline hydrolysis liberates the d-sec-butyl amine for use in preparation of the novel (d)-4-tert-butyl-N-sec-butyl amine-2,6-dinitroaniline. The l-isomer is prepared similarly.

The optically active isomers of this invention are particularly useful because of their unique activity in enzyme catalyzed biological systems.

EXAMPLE VI 4.5 grams (0.11 moles) of sodium hydroxide was dissolved in 100 ml. of methanol. 32.4 grams (0.10 moles) of 4-tert-butyl-2,6-dinitrophenol was dissolved in the resultant solution. 23 grams (0.12 moles) of tosyl chloride was added and the mixture stirred at 35° C for 1.5 hours. The solid was filtered and washed with water to obtain 33 grams (84% yield) of a light yellow tosylate product melting at 124°–130° C.

The optically active amine reactant was then obtained by the following procedure. 135 grams (0.9 moles) of d-(dextrorotatory) tartaric acid was dissolved in 500 ml. of distilled water. 73 grams (1.0 moles) of sec-butylamine (as the racemic mixture) was added slowly with agitation. After complete addition of the d-(dextrorotatory) and l-(levorotatory) sec-butylamine as the racemic mixture, the solution was evaporated to 400 ml. cooled, and the less soluble d-sec-butylamine-d-tartrate was crystallized, filtered and dried in a vacuum dessicator. By repetition of this procedure a sufficient number of times, all of the d-sec-butylamine-d-tartrate was separated out first, followed by the more l-sec-butylamine-d-tartrate. Identity of the two separate optical isomer forms was established by melting point determinations. The d-sec-butylamine and l-sec-butylamine compounds were liberated from their corresponding tartrate salts by distillation from 50% aqueous sodium hydroxide. Identity of these optically active d- and l-sec-butylamine isomers was confirmed by polarimetric measurements of optical rotation.

29.4 grams (0.10 moles) of the tosylate and 14.6 grams (0.20 moles) of either the d- or l-optical isomer of sec-butylamine in 200 ml of water was stirred and heated at reflux for 3 hours. After cooling to room temperature the mixture was filtered and the solid washed with water. The dried product, as either the d- or l- optical isomer of 4-tert-butyl-N-sec-butyl-2,6-dinitroaniline, weighed 23.6 grams (80% yield). Identity of the d- and l- optical isomer forms was confirmed by polarimetric measurements of optical rotation. These gave specific rotations of +1.44 and −1.63, employing a concentration of 0.4 g/ml. of the material dissolved in acetone, using 40 cm tubes, and reading on sodium D.

The following are non-limiting examples of formulations containing the compounds of this invention.

EXAMPLE VII

2 LB/GAL EMULSIFIABLE CONCENTRATE

| Chemical | Lbs. | % by Wt. |
| --- | --- | --- |
| 4-tert-butyl-N-sec-butyl-2,6-dinitroaniline | 2.02 | 23.40 |
| Atlox 3387 | 1.00 | 11.59 |
| Panasol AN-3 | 5.61 | 65.01 |

Specific Gravity: 1.037 at 20° C.
Manufacturing Directions: Combine ingredients and stir to a homogeneous solution.

As exemplified above, the emulsifiable concentrates are formulated by dissolving the herbicidal compound in an organic solvent such as an aromatic oil which is readily dispersed in water, and if desired, one or more co-solvents such as the higher alcohols, ketones, butyrolactone, etc. can be used. Such concentrates are preferably formulated with wetting agents. Any suitable wetting agent either anionic, cationic or non-ionic may be employed.

EXAMPLE VIII

| Granular Chemical | % by Wt. |
| --- | --- |
| 4-tert-butyl-N-sec-butyl-2,6-dinitroaniline | 4.2 |
| Vermiculite, Trenton No. 4 | 95.8 |
| | 100.0 |

| | |
| --- | --- |
| Acetone Solvent | 15.0 |

Manufacturing Directions: The 4-tert-butyl-N-sec-butyl-2,6-dinitroaniline is put into solution with acetone and the solution sprayed onto tumbling vermiculite. The solvent is evaporated off.

EXAMPLE IX

| Liquid Concentrate Chemical | Lbs. | % by Wt. |
| --- | --- | --- |
| 4-tert-butyl-N-sec-butyl-2,6-dinitroaniline | 4.244 | 50.48 |
| Toximul D | 0.420 | 5.00 |
| Dimethylformamide | 0.999 | 11.88 |
| Xylene (0.868 at 20° C.) | 2.745 | 32.64 |
| | 8.408 | 100.00 |

Specific Gravity: 1.010 at 20° C
Manufacturing Directions: Add ingredients and stir until solution is achieved and specific gravity is correct.

The novel compounds of this invention are useful in eliminating germinating and seedling weed grasses and broadleaf weed grasses and broadleaf weeds, regulating plant growth, particularly tobacco sucker control, stimulating plant growth and other uses related and unrelated to the agricultural arts.

More particularly, the compounds are useful in selectively inhibiting the growth of undesirable weed grasses and broadleaf weeds in fields prepared and planted with agronomic crops and providing enhanced crop growth.

The novel herbicidal and plant growth stimulation compounds of this invention are employed by applying a herbicidally effective amount to an area infested with weed grasses or broadleaf weeds in the seed, seedling or germination stage.

The novel compounds of this invention and herbicidal formulations thereof are useful in eliminating weed grasses and broadleaf weeds from crop-bearing soils by preemergence and preferably by preplant incorporated application to areas prepared for planting such crops as corn, beans, potatoes, cotton, sorghum, tomatoes, asparagus, onions, cucurbits, cereal grains, peas, beets, peppers, sunflowers, alfalfa, and related species.

The compounds are also useful when applied post-emergent to the desired species and preferably pre-emergent to the weed species, for example, to turfgrass seedling alfalfa and the like.

It is a particular advantage of the compounds of this invention that the growth of crop plants is not adversely affected by application of the compound at rates sufficient to provide control of weeds. These compounds, and particularly the 4-tert-butyl-N-sec-butyl-2,6-dinitroaniline, have been found to be especially safe to vine crops, such as cucumbers, watermelons, pumpkins, and the like; beans, such as soybeans, dry beans, navy beans, and others; corn, sorghum, potatoes, legumes, such as alfalfa and peas; and other crop species. The unexpected wide margin (3 to 6 more lbs./A difference) between application rate sufficient to destroy weeds and the rate at which even tolerable injury to crops is encountered, is particularly noteworthy, when compared to known dinitroaniline herbicides which generally can be employed only by tolerating acceptable level of crop injury in order to obtain the greater benefits of weed control. In field trails, areas planted with cucumbers, corn and potatoes have shown prosperous and vigorous growth of these crops when treated with amounts of a compound of this invention sufficient to inhibit the germination and growth of most weed species present.

In particular, the compound 4-tert-butyl-N-sec-butyl-2,6-dinitroaniline has been found to produce an enhanced growth effect on desirable crops, particularly cotton, beans (such as soybeans, dry beans, lima beans, etc.), potatoes, melons (such as cantaloupes, watermelons and the like) and other cucurbits (such as cucumbers, squash and the like), and others. This effect has been most noticeable in the warmer climates, especially in areas where soil temperatures are generally about 60° F. or greater.

More particularly, the enhanced growth effect obtained by treatment with 4-tert-butyl-N-sec-butyl-2,6-dinitroaniline appears as a total growth stimulation greater ordinarily that or obtained as the result of eliminating competitive weeds only.

Crops planted in soil treated with 4-tert-butyl-N-sec-butyl-2,6-dinitroaniline exhibit more vigorous healthy growth as well as a significant increase in crop yields which, by comparison to hand weeded controls, have shown to exceed the increased yield effect normally attributable to elimination of competition for nutrients due to the presence of undesirable weed species.

The mechanism by which 4-tert-butyl-N-sec-butyl-2,6-dinitroaniline functions to achieve the enhanced growth effect on desirable crop species, such as cotton, cucurbits, beans and the like, when applied at rates which are toxic to undesirable weed species such as giant foxtail, crabgrass, barnyard grass, Fall Panicum, annual rye and others is not entirely understood, though it can be attributed to a physiological response by the plant in some cases and in other cases, the elimination of one or more agro-climatic lesions, or a combination of these factors.

By agro-climatic lesions is meant such environmental factors normally present in the area of the seed bed as have an adverse but non-toxic effect upon the germinating seed and/or the growing plant such as soil fungi, bacteria, nematodes and the like, as well as other pathogenic substances which might attack either the root system or the plant itself, suppressing the normal growth by weakening the plant or by interfering with the uptake of nutrients or other of the plant's normal growth functions. It includes also such other adverse conditions as temperature, light quality (wave length), photo period (plant response to length of day), humidity, etc.

The growth stimulation achieved by treatments with 4-tert-butyl-N-sec-butyl-2,6-dinitroaniline is manifested not only by increased yield, but by more hardy, vigorous and thriftier plants which are less susceptible to disease and other adverse climatic conditions. By comparison with other known 2,6-dinitroaniline herbicides, plants treated with 4-tert-butyl-N-sec-butyl-2,6-dinitroaniline do not show the root pruning effect characteristic of treatment with the known 2,6-dinitroaniline herbicides. Plants grown in plots treated with 4-tert-butyl-N-sec-butyl-2,6-dinitroaniline have an enhanced root development particularly in the case of the number, size and vigor of the lateral roots. This growth stimulation is also manifested in earlier maturity for such crops as rice. This increased growth stimulation effect observed with 4-tert-butyl-n-sec-butyl-2,6-dinitroaniline is illustrated by the results of field tests described hereinbelow.

In addition to the benefits discussed above, the novel compounds of this invention have produced certain surprising and wholly unexpected results not previously demonstrated with any of the known dinitroaniline herbicide materials.

The compounds of this invention have been shown to be particularly effective against rhizome Johnson grass, a perennial species, and in this and other of its herbicidal applications, it has been found useful when applied in the fall for weed control during the subsequent planting and growing season. In the case of fall applications, it is, of course, desirable to utilize greater amounts and generally from about 3 to 12 pounds per acre depending upon the type of weed infestation, soil type and other factors.

When applied to turfgrasses in granular form, it has been found to have a surprisingly beneficial effect as a preemergent crabgrass control agent. In this case, the granular form has been found to be particularly more beneficial than the liquid application. And with granular applications, later seeded turfgrass has shown tolerance and germinated satisfactorily, after application of the herbicide where the herbicide still actively prevented emergence of crabgrass.

The novel compounds of this invention have surprisingly also shown post emergence herbicidal effectiveness against various weed species.

The novel compounds of this invention have also shown a special herbicidal effectiveness against the parasitic weed Dodder in alfalfa, being able to provide 100% control of that weed without any corresponding injury to the alfalfa crop, whereas prior art dinitroanilines do not give effective control of Dodder.

Dodder is a particularly serious problem to the farmer of crops, such as, alfalfa, cranberries, and clover, although not limited to such crops. Seed from Dodder infested fields are practically unsalable. A crop from a Dodder infested field cannot even be harvested and fed to animals for the Dodder seeds often pass uninjured through the digestive tract of the animal and thus infest other fields.

The compounds of this invention, particularly 4-tert-butyl-N-sec-butyl-2,6-dinitroaniline, unlike the prior art compounds, have been found to be particularly effective for preemergence control of Dodder, and to a certain extent, post-emergence control.

The novel compounds of this invention have further demonstrated a surprising effectiveness for controlling pest type fish, whereas the prior art dinitroanilines do not demonstrate this effectiveness for control.

As discussed above, the compounds of this invention do not exhibit the root pruning effect characteristic of known 2,6-dinitroaniline herbicide materials. Not only do the compounds of this invention not have a root pruning effect, but they display a positive enhancement of root development, when compared to other known 2,6-dinitroaniline herbicidal materials.

The 4-tert-buty-N-sec-butyl-2,6-dinitroaniline, in particular, exhibits a wider safety margin between the rate that will injure plants of desirable crop species and rates at which total weed control can be obtained.

This property is particularly important in plants grown for seed production, where the low acreage of crop species permits the use of high rates of herbicidal materials, 6 to 8 pounds per acre or greater which rates could not ordinarily be used as an economic treatment for ordinary field crops. In this way the compound can be used to give complete control of noxious weeds, particularly grasses, without injury to the crops. This wide safety margin also permits the use of higher than normal rates for elimination of hard-to-kill weed species, such as morning glory and teaweed, as well as black nightshade and cow cockle. By using this high rate for one or two seasons, the weed population of these difficult to control weeds can be reduced to levels which are not detrimental to crops for several ensuing growing seasons under ordinary herbicide treatment.

In particular, the compound 4-tert-butyl-N-sec-butyl-2,6-dinitroaniline has been found to be particularly useful in controlling weeds in areas planted with such desirable crop species as beans, for example, soybeans, lima beans, dry beans, southern peas, bush or snap beans, pinto beans, kidney beans, navy beans, and the like, peanuts, tomatoes, cucurbits, such as cucumbers, watermelons, musk melons, cantaloupes, honeydews, squash, pumpkin and the like, peppers, tobacco, rice, particularly transplanted rice, sweet potatoes, white or Irish potatoes, yams, safflower, sunflower, castor beans, okra, sugar beets (application should be made as incorporated treatments after the beets are 4 to 6 inches tall or by preplant incorporation before the beets are planted), sugarcane (applied after planting cane with shallow incorporation), cruciferae, such as cabbage, broccoli, cauliflower; brussel sprouts, kale, rape, turnips, mustard, rutabaga and the like, umbilliferae, such as carrots, parsnips, dill, celery, parsley and the like, turfgrasses and ornamentals, particularly annually flowering or established perennials in which case the compound is worked into the soil in the area surrounding the ornamental plant.

The 4-(tert-butyl)-N-(sec-butyl)-2,6-dinitroaniline compound can be used for weed control in orchards by discing the compound into the orchard to give excellent weed control for established fruit and nut trees. The compound is particularly effective for controlling such grasses as crabgrass, foxtail, barnyard grass, Fall panicum, Johnson grass, cheatgrass, black grass (*Alopecurus*), spangle top (*Brachiaria*), red rice, witch grass, silver crab, annual bluegrass (*Poa annua*), annual ryegrass, and many of the broadleaf weeds, including pigweed, Florida pusley, chickweed, poor Joe, lambsquarter, carpet weed, teaweed, morning glory, Kochia, smartweed and others.

This compound can further be used to kill or control weeds such as black nightshade and teaweed at rates selective to crops such as beans. Such control is not possible with known 2,6-dinitroaniline herbicide materials, such as trifluralin and nitralin. This ability of the 4-tert-butyl-N-sec-butyl-2,6-dinitroaniline to produce desirable plant growth in crop species together with other peculiar beneficial results obtained with this compound suggest that, while its exact mode of action is not entirely understood, it does possess highly unique biological characteristics.

The following Evaluations are provided to illustrate the uses of the novel compounds of this invention, and are not to be construed as limiting the scope of uses and properties of these compounds.

EVALUATION 1

HERBICIDAL ACTIVITY AND CROP SELECTIVITY OF 4-Bu-N-R-2,6-DINITROANILINES

Test flats were prepared from soil blended with fertilizer, sand and peat moss and prepared for seeding in replicates of about 10 inches by about 20 inches and about 2 to 3 inches deep. The flats were seeded with the test species in rows, covered with soil and watered till moist to feel. The test chemical was sprayed on the surface of the flats before seeding, and incorporated into top 1 inch of soil. The results were observed by comparison to controls 4 to 5 weeks after seeding. The percent control in the case of grass weeds and broadleaf weeds is based upon the number and vigor of weeds emerging in the treated flat as compared to the untreated controls. Percent injury in the case of crop plants represents the extent of growth inhibition that can be observed by comparison of the crop plants in the treated soil and those in the untreated soil.

Table II

| | 2,6-DINITROANILINE DERIVATIVES | | | | | | | | | | | | |
|---|---|---|---|---|---|---|---|---|---|---|---|---|---|
| Bu R | Bu | t-Bu Me | t-Bu Et | t-Bu i-Pr | t-Bu n-Bu | t-Bu s-Bu | t-Bu t-Bu | t-Bu t-Pe | t-Bu i-Pe | t-Bu allyl | t-Bu methoxy propyl | t-Bu dimethoxy ethyl | t-Bu ⬡- |
| Compound No. | 1 | 2 | 3 | 4 | 5 | 6 | 7 | 8 | 9 | 10 | 11 | 12 | |
| Rate No./A | 16 | 16 | 8 | 8 | 8 | 8 | 8 | 8 | 8 | 8 | 8 | 8 | |
| Test Plant | | | | | | | | | | | | | |
| Downy Brome | 10 | 100 | 100 | 60 | 100 | 100 | 100 | 100 | 100 | 100 | 100 | 60 | |
| Chickweed | 0 | 100 | 100 | 30 | 100 | 100 | 100 | 90 | 100 | 100 | 30 | 0 | |
| Wildoats | 0 | 100 | 100 | 70 | 90 | 100 | 100 | 90 | 100 | 50 | 10 | 80 | |
| Barnyard-grass | 10 | 100 | 100 | 75 | 100 | 100 | 90 | 95 | 100 | 95 | 50 | 70 | |
| Foxtail | 15 | 100 | 100 | 80 | 100 | 100 | 100 | 100 | 100 | 100 | 90 | 40 | |
| Morning-glory | 0 | 15 | 30 | 0 | 85 | 0 | 0 | 0 | 30 | 0 | 20 | 0 | |
| Velvet-leaf | 30 | 10 | 25 | 0 | 80 | 0 | 10 | 80 | 0 | 0 | 0 | 0 | |
| Johnson grass | 10 | 100 | 100 | 85 | 100 | 100 | 100 | 95 | 100 | 90 | 30 | 70 | |
| Pigweed | 20 | 100 | 100 | 95 | 100 | 90 | 90 | 95 | 100 | 70 | 80 | 30 | |
| Lambs-quarter | 20 | 100 | 100 | 45 | 100 | 95 | 50 | 0 | 100 | 95 | 50 | 100 | |
| Nutsedge | 10 | 0 | 100 | 100 | 100 | 0 | 0 | 0 | 0 | 0 | 0 | 0 | |
| Alopecurus | 20 | 100 | 100 | 100 | 100 | 100 | 100 | 100 | 100 | 100 | 100 | 100 | |
| Curled dock | 0 | 100 | 95 | 95 | 40 | 50 | 100 | 95 | 100 | 90 | 85 | 85 | |
| Crabgrass | 30 | 100 | 100 | 100 | 100 | 100 | 100 | 100 | 100 | 100 | 100 | 95 | |

2,6-DINITROANILINE DERIVATIVES

Table II-continued

| R | Bu n-hexyl | t-Bu cyclopropyl | t-Bu cyclopropyl methyl | s-Bu Me | s-Bu Et | s-Bu i-Pr | s-Bu s-Bu | s-Bu n-Bu | s-Bu t-Bu | s-Bu cyclohexyl | s-Bu dimethoxyethyl | s-Bu methoxypropyl |
|---|---|---|---|---|---|---|---|---|---|---|---|---|
| Compound No. | 13 | 14 | 15 | 16 | 17 | 18 | 19 | 20 | 21 | 22 | 23 | 24 |
| Rate No./A | 16 | 8 | 8 | 8 | 8 | 8 | 8 | 8 | 8 | 8 | 8 | 8 |
| Test Plant | | | | | | | | | | | | |
| Downy Brome | 40 | 40 | 0 | 100 | 100 | 100 | 100 | 100 | 100 | 30 | 0 | 60 |
| Chickweed | 10 | 80 | 100 | 100 | 100 | 100 | 100 | 90 | 100 | 0 | 0 | 20 |
| Wildoats | 50 | 80 | 0 | 20 | 100 | 100 | 100 | 90 | 90 | 90 | 15 | 0 |
| Barnyardgrass | 65 | 30 | 0 | 10 | 100 | 100 | 100 | 90 | 100 | 70 | 30 | 80 |
| Foxtail | 70 | 95 | 0 | 90 | 100 | 100 | 100 | 95 | 100 | 95 | 40 | 60 |
| Morningglory | 0 | 0 | 0 | 0 | 20 | 30 | 40 | 0 | 0 | 0 | 10 | 40 |
| Velvetleaf | 0 | 0 | 0 | 10 | 0 | 40 | 40 | 0 | 40 | 0 | 10 | 80 |
| Johnson grass | 70 | 0 | — | 90 | 100 | 100 | 100 | 100 | 100 | 70 | 30 | 95 |
| Pigweed | 85 | 0 | 40 | 100 | 100 | 100 | 100 | 100 | 100 | 70 | 100 | 50 |
| Lambsquarter | 30 | — | — | 100 | 100 | 100 | 100 | 10 | 90 | 20 | 0 | 60 |
| Nutsedge | 0 | 0 | 0 | 70 | 100 | 10 | 0 | 0 | 0 | 0 | 0 | 0 |
| Alopecurus | 90 | 100 | — | 95 | 100 | 100 | 100 | 100 | 100 | 100 | 40 | 100 |
| Curled dock | 40 | 90 | — | 40 | 100 | 100 | 100 | 90 | 100 | 70 | 30 | 100 |
| Crabgrass | 90 | 100 | 85 | 100 | 100 | 100 | 100 | 100 | 100 | 95 | 90 | 100 |

Table III

HERBICIDAL ACTIVITY AND CROP SELECTIVITY OF COMPOUNDS

| Compound No. | 2 | 3 | 5 | 6 | 9 | 17 | 18 | 19 | 21 |
|---|---|---|---|---|---|---|---|---|---|
| Rate No./A | 2 | 1 | 1 | 2 | 1 | 1 | 1 | 1 | 1 |
| Test Plant | | | | | | | | | |
| Pigweed | 95 | 100 | 100 | 40 | 15 | 15 | 30 | 85 | 0 |
| Foxtail | 95 | — | 100 | 45 | — | — | — | — | — |
| Wheat | 15 | 30 | 70 | 10 | 20 | 10 | 10 | 0 | 0 |
| Crabgrass | 100 | 100 | 100 | 100 | 80 | 80 | 100 | 100 | 25 |
| Curled Dock | 15 | 45 | 85 | 0 | 35 | 30 | 70 | 45 | 0 |
| Corn | 20 | 20 | 20 | 20 | 25 | 0 | 20 | 10 | 0 |
| Velvetleaf | 0 | 0 | 30 | 0 | 0 | 0 | 0 | 0 | 0 |
| Johnson grass | 45 | — | 100 | 45 | — | — | — | — | — |
| Soybeans | 0 | 0 | 0 | 0 | 0 | 0 | 0 | 0 | 0 |
| Barnyardgrass | 45 | 100 | 100 | 45 | 45 | 80 | 100 | 100 | 30 |
| Lambsquarter | 10 | — | 45 | 0 | — | — | — | — | — |
| Sugar Beets | 0 | 20 | 20 | 0 | 0 | 0 | 0 | 0 | — |
| Alfalfa | 0 | 15 | 20 | 0 | 0 | 0 | 15 | 10 | 0 |
| Fall Penicum | 95 | 100 | 100 | 25 | 100 | 90 | 100 | 100 | 45 |
| Cheatgrass | 90 | 100 | 80 | 0 | 80 | 70 | 85 | 100 | 0 |
| Cotton | 0 | — | 0 | 0 | — | — | — | — | — |
| Alopecurus | 100 | 100 | 100 | 90 | 95 | 95 | 100 | 100 | 80 |
| Chickweed | 25 | — | 95 | 0 | — | — | — | — | — |
| Cucumbers | 30 | 0 | 0 | 0 | 0 | 0 | 0 | 0 | 0 |
| Muskmelon | 0 | — | 0 | 0 | — | — | — | — | — |
| Morning Glory | 15 | 0 | 40 | 0 | 0 | 0 | 20 | 0 | 0 |
| Wild Mustard | 10 | — | 10 | 0 | — | — | — | — | — |
| Rice | 25 | 100 | 40 | 15 | 100 | 100 | 100 | 100 | 70 |
| Annual Rye | 90 | 100 | 90 | 30 | 85 | 90 | 100 | 100 | 30 |
| Cocklebur | — | — | 0 | — | 0 | 0 | 0 | — | 0 |
| Y. Nutsedge | 0 | — | — | 0 | — | — | — | — | — |
| Tomatoes | 0 | 0 | 20 | 0 | 0 | 0 | 0 | 0 | 0 |
| Onions | 0 | 95 | 20 | 0 | 15 | 0 | 25 | 20 | 0 |
| Giant Foxtail | — | 100 | — | — | 40 | 35 | 100 | 100 | 35 |
| B.Nightshade | — | 0 | — | — | 0 | 0 | 10 | 0 | 0 |
| Jimson | — | 0 | — | — | 0 | 0 | 0 | 0 | 0 |
| Coffeeweed | — | 100 | — | — | 0 | 0 | 25 | 25 | 0 |
| Chrysanthemum | — | 85 | — | — | 0 | 0 | 0 | 10 | 0 |
| Galium | — | 0 | — | — | 0 | 0 | 0 | 0 | 0 |
| Matricaria | — | 70 | — | — | 0 | 0 | 20 | 0 | 0 |
| Teaweed | — | — | — | — | 0 | — | 0 | — | 0 |
| Wild Oats | — | 100 | — | — | 40 | 25 | 100 | 10 | 0 |

Table IV

CROP SELECTIVITY OF COMPOUNDS % INJURY

| Compound No. | No./A | Soybeans | Tomatoes | Cotton | Corn | Sugar Beets | Cucumbers |
|---|---|---|---|---|---|---|---|
| 2 | 1 | 0 | 0 | 0 | 30 | 0 | 0 |
| 3 | 1 | 0 | 0 | 0 | 20 | 20 | 0 |

Table IV-continued

CROP SELECTIVITY OF COMPOUNDS
% INJURY

| Compound No. | No./A | Soybeans | Tomatoes | Cotton | Corn | Sugar Beets | Cucumbers |
|---|---|---|---|---|---|---|---|
| 5 | 1 | 0 | 20 | 0 | 20 | 20 | 0 |
| 6 | 2 | 0 | 0 | 0 | 20 | 0 | 0 |
| 9 | 1 | 0 | 0 | 0 | 20 | 0 | 0 |
| 17 | 1 | 0 | 0 | 0 | 0 | 0 | 0 |
| 18 | 1 | 0 | 0 | 0 | 20 | 0 | 0 |
| 19 | 1 | 0 | 0 | 0 | 0 | 0 | 0 |
| 21 | 1 | 0 | 0 | — | 0 | 0 | 0 |
| 7 | 1 | 0 | 0 | — | 0 | 0 | 0 |
| 10 | 4 | 0 | 0 | 0 | 0 | 0 | 0 |
| 11 | 1 | 0 | 0 | — | 0 | 0 | 0 |
| 14 | 2 | 0 | 0 | 0 | 0 | 0 | 0 |
| 16 | 1 | 0 | 0 | — | 0 | 0 | 0 |

EVALUATION 2

FIELD TEST SELECTIVITY OF 4-TERT-BUTYL-N-SEC-BUTYL-2,6-DINITROANILINE

In a field test, treatments were sprayed August 6, at 17 gpa. All chemicals in one replication were incorporated 2 inches with a power-drive tillrovator. The 10 crops and also four weed species, were planted the next day and evaluated one month later on September 5. Subsurface soil was dry. There were two inches of rain during the first three weeks after treatment (1 inch plus 1 inch of irrigation two days after treatment).

Table V

RESPONSE OF VARIOUS CROPS AND WEEDS TO PREPLANT INCORPORATED 4-TERT-BUTYL- N-SEC-BUTYL-2,6-DINITROANILINE

| Rate No./A Tillrovated | 1 % Control or Injury |
|---|---|
| Test Plant | |
| Cotton (DPL smoothleaf) | 0 |
| Soybeans (Lee) | 0 |
| Southern peas (Growder) | 0 |
| Cantaloupe | 0 |
| Cucumbers | 0 |
| Snapbeans | 0 |
| Seedling Johnson Grass | 100 |
| Crabgrass | 100 |
| Brachiaria | 100 |
| Morning glory | 75 |
| Coffeeweed | 80 |

The novel herbicidal compounds of this invention can be conveniently applied as preemergence herbicides in either liquid or granular form and are preferably incorporated into the soil at planting. The compounds are generally crystalline materials with only slight solubility in water. Where liquid formulations are desired they can be compounded in the form of wettable powders or emulsifiable concentrates which can be readily diluted with water prior to application. The compounds can also be applied in the form of herbicidal dusts or combined with fertilizers or other herbicidal substances such as the N,N-dialkylthio carbamates. Suitable granular compositions can be readily prepared by dissolving the herbicidal substance in a light organic solvent such as acetone which is then sprayed on a carrier such as attapulgite clay, vermiculite, ground corncob, etc. and the solvent removed by evaporation. As noted above the granular formulations and in particular a granular formulation of 4-tert-butyl-N-sec-butyl-2,6-dinitroaniline is especially useful as a preemergence crabgrass killer. Accordingly this invention also encompasses granular formulations of the novel compounds of this invention together with a granular carrier material which can if desired also be a granular fertilizer material such as ammonium nitrate, urea prills, etc. Suitable granular formulations are those containing from about 2 to 20% by weight of active ingredient uniformly dispersed on a dry granular carrier material such as attapulgite clay, vermiculite or ground corn-cobs. The granular formulations have been found particularly well suited to preemergence application to turf grass for control of crabgrass as shown by the following test results.

EVALUATION 3

PREEMERGENCE CRABGRASS WITH GRANULAR COMPOSITION OF 4-TERT-BUTYl-N-SEC-BUTYL-2,6-DINITROANILINE

In early spring, test area was verticut and over-seeded with both smooth and hairy crabgrass. All treatments were applied on May 15, using a Lawn-Beauty granular applicator with a bin vibrator attached to give uniform application. With this procedure, a minimum of four passes was made to apply chemical on plots measuring 4 feet × 12 feet. Actual treatment area was 3 feet × 12 feet.

Rainfall of 0.04 inch fell on plots the same day as application; first appreciable rainfall occurred three days after treatment, recorded at 0.60 inch.

Table VI

| Chemical | Rate lb/A ai | % CRABGRASS CONTROL - PREEMERGENCE | | | | | | | | | | | |
|---|---|---|---|---|---|---|---|---|---|---|---|---|---|
| | | July 9 | | | | July 24 | | | | September 4 | | | |
| | | I | II | III | Avg. | I | II | III | Avg. | I | II | III | Avg |
| 4-tert-butyl-N-sec-butyl-2,6-dinitro-aniline | 1 | 80 | 100 | 75 | 85 | 60 | 80 | 40 | 60 | 35 | 40 | 10 | 28 |
| ,, | 2 | 97 | 95 | 95 | 96 | 90 | 75 | 70 | 78 | 70 | 85 | 60 | 72 |
| ,, | 4 | 100 | 100 | 100 | 100 | 100 | 100 | 100 | 100 | 98 | 100 | 95 | 98 |
| ,, | 8 | 100 | 100 | 100 | 100 | 100 | 100 | 100 | 100 | 100 | 100 | 98 | 99 |

TURF TOLERANCE - % INJURY

Table VI-continued

| Chemical | Rate lb/A ai | % CRABGRASS CONTROL - PREEMERGENCE | | | | | | | | September 4 | | | |
| --- | --- | --- | --- | --- | --- | --- | --- | --- | --- | --- | --- | --- | --- |
| | | July 9 | | | | July 24 | | | | | | | |
| | | I | II | III | Avg. | I | II | III | Avg. | I | II | III | Avg |
| 4-tert-butyl-N-sec-butyl-2,6-dinitro-aniline | 1 | 0 | 0 | 0 | 0 | 0 | 0 | 0 | 0 | 0 | 0 | 0 | 0 |
| " | 2 | 0 | 0 | 0 | 0 | 0 | 0 | 0 | 0 | 0 | 0 | 0 | 0 |
| " | 4 | 0 | 0 | 0 | 0 | 0 | 0 | 0 | 0 | 0 | 0 | 0 | 0 |
| " | 8 | 0 | 0 | 0 | 0 | 0 | 0 | * | * | 0 | 0 | 0 | 0 |

*= Trace Injury

EVALUATION 4

TURFGRASS SEED TOLERANCE TO 4-TERT-BUTYL-N-SEC-BUTYL-2,6-DINITROANILINE

The following test demonstrates the tolerance of turfgrass seed to the novel compounds of this invention, applied to a given area prior to seeding for the purpose of controlling weeds such as crabgrass.

The test plots were treated with a granular formulation of 4-tert-butyl-N-sec-butyl-2,6-dinitroaniline on May 7, and verticut and successfully overseeded with a mixture of common bluegrass and Pennlawn red fescue in Augest. This was 101 days after the herbicide application, and during the normal fall seeding time interval. The turfgrass germinated satisfactorily, and as shown below, in all treated plots the bluegrass — fescue stand was greater than in the untreated ones. The 4-tert-butyl-N-sec-butyl-2,6-dinitroaniline actively prevented emergence of crabgrass in the test plots throughout the summer growing season. Moreover, in greenhouse persistence studies using the granular formulation applied to the test plots as described above, yellow foxtail (*Setaria lutenscens*) and silver crabgrass (*Eleusine indica*) in flats of unsterilized soil treated at the 4 lb/A rate were prevented from emerging up to 120 days, a period significantly in excess of the 101 day interval involved in this test.

Table VII

| | Rate lb/A | Average Number Seedlings /4" Plug* |
| --- | --- | --- |
| 4-tert-butyl-N-sec-butyl-2,6-dinitroaniline | 0 | 15 |
| 4-tert-butyl-N-sec-butyl-2,6-dinitroaniline | 2 | 19 |
| 4-tert-butyl-N-sec-butyl-2,6-dinitroaniline | 4 | 18 |
| 4-tert-butyl-N-sec-butyl-2,6-dinitroaniline | 6 | 33 |
| 4-tert-butyl-N-sec-butyl-2,6-dinitroaniline | 8 | 24 |

*Three 4" plug samples each counted from 6 replications on September 2.

EVALUATION 5

CONTROL OF *Poa annua* IN TURF WITH 4-TERT-BUTYL-N-SEC-BUTYL-2,6-DINITROANILINE Satisfactory control of *Poa annua*, an annual bluegrass weed in turf which has long proven difficult to control with herbicides, was achieved in the following text.

Treatments of 4-tert-butyl-N-sec-butyl-2,6-dinitroaniline were applied on October 31 and on the following April 15 to established turf.

Table VIII

| | Rate lb/A | Time of Treatment | % Control of Poa Annua |
| --- | --- | --- | --- |
| 4-tert-butyl-N-sec-butyl-2,6-dinitroaniline | 4 | Fall | 80 |
| 4-tert-butyl-N-sec-butyl-2,6-dinitroaniline | 8 | Fall | 85 |
| 4-tert-butyl-N-sec-butyl-2,6-dinitroaniline | 12 | Fall | 50 |
| Check | 0 | Fall | 0 |
| Combined treatment: | | | |
| 4-tert-butyl-N-sec-butyl-2,6-dinitroaniline | 4 | Fall | 90 |
| 4-tert-butyl-N-sec-butyl-2,6-dinitroaniline | 4 | Spring | |

EVALUATION 6

4-TERT-BUTYL-N-SEC-BUTYL-2,6-DINITROANILINE POSTEMERGENCE CONTROL OF BARNYARDGRASS IN RICE

Excellent postemergence control of barnyardgrass in rice was obtained in the following test:

Rice of the Starbonnet variety was planted during the first week in July with application of the herbicide on July 22. The test plot area was flooded 24 hours after treatment. The test was replicated three times, and evaluations were made on October 8.

Table IX

| Replication No. | lbs/A | Rate | % Control of Barnyardgrass |
| --- | --- | --- | --- |
| 1 | 4-tert-butyl-N-sec-butyl-2,6-dinitro-aniline | 2 | 45 |
| | | 3 | 50 |
| | | 4 | 75 |
| | Check | 0 | 0 |
| 2 | 4-tert-butyl-N-sec-butyl-2,6-dinitro-aniline | 2 | 30 |
| | | 3 | 65 |
| | | 4 | 65 |
| | Check | 0 | 0 |
| 3 | 4-tert-butyl-N-sec-butyl-2,6-dinitro-aniline | 2 | 55 |
| | | 3 | 75 |
| | | 4 | 95 |
| | Check | 0 | 0 |

As has been shown above, the novel compounds of 4-tert-butyl-N-sec-butyl-2,6-dinitroaniline are safe to rice and, in addition to preplant incorporation treatments, can, in certain cases, be employed as preemergence herbicides such as in transplanted rice paddies. In this, as well as the preplant incorporation treatments, the compounds of this invention show notably less soil persistence than have known dinitroaniline herbicides, rendering them more desirable in terms of undesirable residues.

EVALUATION 7

PREEMERGENCE CONTROL OF DODDER IN ALFALFA WITH 4-TERT-BUTYL-N-SEC-BUTYL-2,6-DINITROANILINE

In this test, 4-tert-butyl-N-sec-butyl-2,6-dinitroaniline was applied as a preemergence treatment for the control of Dodder (*Cuscuta campestris*) in alfalfa. The alfalfa crop (*cayauga*) was planted and the herbicide treatment applied together on May 26. The herbicide was applied preemergence to both the alfalfa crop and the Dodder weed. The test plots were evaluated on June 30, and the test results taken from an average of three replications for each of the rates applied.

Table X

PERCENT CONTROL OF DODDER IN ALFALFA WITH 4-TERT-BUTYL-N-SEC-BUTYL-2,6-DINITROANILINE

| Preemergence: | Rate lb/A | Alfalfa Injury | % Control of Dodder |
| --- | --- | --- | --- |
| 4-tert-butyl-N-sec-butyl-2,6-dinitroaniline | 1 | 0 | 92 |
| 4-tert-butyl-N-sec-butyl-2,6-dinitroaniline | 2 | 0 | 100 |
| 4-tert-butyl-N-sec-butyl-2,6-dinitroaniline | 3 | 0 | 100 |

EVALUATION 8

POSTEMERGENCE CONTROL OF DODDER IN ALFALFA WITH 4-TERT-BUTYL-N-SEC-BUTYL-2,6-DINITROANILINE

Excellent postemergence control of Dodder in alfalfa was obtained in the following test.

The treatments with 4-tert-butyl-N-sec-butyl-2,6-dinitroaniline were made postemergence, and at the time of spraying the alfalfa was in the 4th trifoliate stage and the Dodder had emerged and was about an inch in length. The results of the test were recorded 8 days after the treatment was applied.

Table XI

| Postemergence: | Rate lb/A | % Control of Dodder |
| --- | --- | --- |
| 4-tert-butyl-N-sec-butyl-2,6-dinitroaniline | 1 | 84 |
| 4-tert-butyl-N-sec-butyl-2,6-dinitroaniline | 2 | 96 |

EVALUATION 9

AQUATIC WEED CONTROL

The compounds of this invention have also shown aquatic herbicidal activity as demonstrated by the following test results.

A container having growing specimens of the aquatic weed species in water is treated by adding 4-tert-butyl-N-sec-butyl-2,6-dinitroaniline dissolved in a suitable solvent at rates sufficient to give a final concentration of 5 ppm or 10 ppm, as indicated. Effect on the weeds is noted and recorded about three weeks after application.

Table XII

AQUATIC WEED HERBICIDAL ACTIVITY

| | | % Control | |
| --- | --- | --- | --- |
| Compound No. | Concentration ppm | Duckweed | Salvinia |
| 2 | 10 | 90 | 100 |
| 3 | 5 | 80 | 80 |
| 4 | 5 | 50 | 70 |
| 5 | 5 | 100 | 100 |
| 6 | 5 | 90 | 60 |
| 9 | 5 | 100 | 100 |
| 10 | 10 | 50 | 60 |
| 12 | 5 | 0 | 70 |
| 14 | 5 | 30 | 60 |
| 16 | 5 | 0 | 30 |
| 17 | 5 | 70 | 100 |
| 18 | 5 | 90 | 90 |
| 19 | 5 | 90 | 30 |
| 21 | 5 | 30 | 110 |

As disclosed above, the novel compounds of this invention have shown growth regulant activity when applied to plants such as tobacco and similar species. The novel compounds of this invention, when used in the control of tobacco suckers, are applied after topping of the tobacco and preferably applied to the stem area of the tobacco plant. This can be conveniently accomplished by spraying the entire plant. The compounds of this invention are applied to topped tobacco plants by spraying at rates of 1 to 6 lbs/acre, and preferably at about 2 lbs/acre, preferably in combination with a suitable surfactant material. The surfactant is present in an amount between about 0.05 to about 2% by weight of active ingredient, that is, 4-tert-butyl-N-sec-butyl-2,6-dinitroaniline.

The combination of 4-tert-butyl-N-sec-butyl-2,6-dinitroaniline and surfactant is preferably applied by spraying in about 50 to 200 gallons of water per acre. Suitable surfactants are the known anionic or nonionic and particularly the nonionic surfactants customarily employed in formulating herbicidal materials. Examples of anionic surfactants are the sulfonates such as the alkylbenzene sulfonates, the sulfated surfactants such as sulfated alcohols, acids, amides, esters, sulfated natural fats and oils, etc.; the phosphate esters such as alkyl polyphosphate surfactants; suitable nonionic materials include the polyoxyethylene surfactants such as the ethoxylated alkyl phenols, the ethoxylated aliphatic alcohols, etc. and the carboxylic esters such as eg. polyethylene glycol esters, polyoxyethylene fatty acid esters; and others.

The effect of the compounds of this invention for inhibition of tobacco suckers is illustrated by the following field tests.

EVALUATION 10

TOBACCO GROWTH REGULANT EFFECTS

Pennbel tobacco plants were transplanted to the field on June 11 with a mechanical transplanter. They were treated August 12 immediately after plants were hand topped down to the first 6 inches wide leaf and suckers over 1 inch long were removed. Plants had just started to bloom. Plants received 0.5 inches overhead irrigation just after spraying and 15.9 inches of rain and irrigation for the duration of the test. Observations were made on September 29.

Excellent tobacco sucker control was obtained with 4-tert-butyl-N-sec-butyl-2,6-dinitroaniline + Triton X-100 (2 lb/A + 0.1%); control equalled that of MH-30 at 3 lb/A. Increasing the spray volume from 100 to 150 gal/A with 4-tert-butyl-N-sec-butyl-2,6-dinitroaniline alone improved sucker control. 4-tert-butyl-N-sec-butyl-2,6-dinitroaniline + 1-Decanol + Triton X-100 (1 lb/A + 1% + .1%) was superior to 4-tert-butyl-N-sec-butyl-2,6-dinitroaniline alone at 1 or 2 lb/A. Alone, 1 Decanol + Triton X-100 (1% − 2% + 0.1%) had no effect on sucker growth. No injury was noted from any treatment.

held at 20–25 pounds. Weather conditions at treatment time were clear, 85°–90° F., 3–5 mph wind, medium relative humidity. Final observations were taken on September 11, 24 days after treatments were applied. Readings are averages of three replications totaling 15 plants per treatment.

Table XV

TOBACCO SUCKER CONTROL WITH
4-TERT-BUTYL-N-SEC-BUTYL-2,6-DINITROANILINE

| Chemical | Rate lb/A | Percent Control* No Surfactant 100 gpa | 150 gpa | 0.1 % Triton X-100 100 gpa | 150 gpa |
|---|---|---|---|---|---|
| 4-tert-butyl-N-sec-butyl-2,6-dinitroaniline | 1.0 | 29 | 21 | 81 | 75 |
|  | 1.5 | 40 | 58 | 91 | 86 |
|  | 2.0 | 57 | 68 | 88 | 92 |
|  | 3.0 | 76 | 84 | 90 | 99 |

*Percent Control - percent by which treatment reduced sucker green weight compared with topped, but not suckered check.

Effectiveness of the sucker control shown above is revealed by the following data comparing sucker number and weight for the treated tobacco plants with that for the check plants.

Table XIII

TOBACCO SUCKER CONTROL WITH
4-TERT-BUTYL-N-SEC-BUTYL-2,6-DINITROANILINE

| Chemical | Rate lb/A | % Control* 150 gpa | % Reduction** |
|---|---|---|---|
| 4-tert-butyl-N-sec-butyl-2,6-dinitroaniline | 1.0 | 15 | 10 |
| '' | 2.0 | 60 | 93 |

Table XVI

COMPARISON OF SUCKERS FROM CHECK PLANTS
AND THOSE TREATED WITH
4-TERT-BUTYL-N-SEC-BUTYL-2,6-DINITROANILINE
(150 GPA)

| Chemical | Rate lb/A | No Surfactant Sucker Wt/Plant (ozs) | Number Suckers/ Plant | Indiv. Sucker Wt (ozs) | 0.1 % Triton X-100 | | |
|---|---|---|---|---|---|---|---|
| 4-tert-butyl-N-sec-butyl-2,6-dinitroaniline | 1.0 | 28.0 | 7.0 | 4.0 | 9.0 | 4.6 | 2.0 |
|  | 1.5 | 14.8 | 5.1 | 2.9 | 5.1 | 2.1 | 2.4 |
|  | 2.0 | 11.5 | 4.9 | 2.4 | 2.7 | 1.9 | 1.4 |
|  | 3.0 | 5.8 | 2.9 | 2.0 | 0.3 | 0.5 | 0.6 |
| Check | — | 35.6 | 13.5 | 2.6 | — | — | — |

It can thus be clearly seen that 4-tert-butyl-N-sec-butyl-2,6-dinitroaniline exerts a pronounced growth regulant effect on tobacco by inhibiting the growth of lateral buds or suckers on such plants.

Table XIV

TOBACCO SUCKER CONTROL WITH
4-TERT-BUTYL-N-SEC-BUTYL-2,6-DINITROANILINE WITH ADDITIVES

| Chemical | Rate lb/A | % Control* 100 gpa Plus .1 % Triton X-100 + 100 gpa | % Reduct.** | % Control* 150 gpa Plus 1 % Decanol + .1 % X-100 + 100 gpa | % Reduct.** |
|---|---|---|---|---|---|
| 4-tert-butyl-N-sec-butyl-2,6-dinitroaniline | 1.0 | 65 | 55 | 78 | 73 |
| '' | 2.0 | 98 | 98 | — | — |

*Reduction in number of suckers over 4" in length.
**Decrease in length of suckers on the plants.

EVALUATION 11

Tobacco plants of the Pennbel variety were transplanted to the field on June 10, with a mechanical transplanter. All plants received starter solution plus chlordane for cutworm control. On August 17, all plants were hand-topped, removing all growth to the first leaf being 6 inches wide. All suckers over 1 inch in length were removed at this time. On August 18, all treatments were applied. A single adjustable cone nozzle, set for a very coarse spray, was used with pressure

EVALUATION 12

THE EFFECT OF
4-(t-BUTYL)-N-(SEC-BUTYL)-2,6-DINITROANILINE ON THE GROWTH OF COTTON, MELONS, TOMATOES AND CUCUMBERS

The plant growth regulating properties of the novel compounds of this invention, also takes the form of an ability to stimulate the growth of various crop plants.

Plants were grown in plastic pots in the greenhouse. There were five replications of one pot each. After spraying, the chemical was thoroughly mixed and incorporated into the soil with a mechanical mixer.

Seeds were planted ½ inch deep. The soil used would be classified as heavy soil.

The sprayer was equipped with an 8002 Tee Jet nozzle and delivered 40 gal. spray solution per acre.

Treated pots were watered by subirrigation to avoid any loss of chemical by leaching.

The trial was run in two phases. One lot of treated soil was planted immediately. A second lot of treated soil was retained and planted after three weeks.

Growth stimulation was observed and measured by comparison with the same crops grown in untreated soil.

Table XVII

EFFECT OF 4-(t-BUTYL)-N-(SEC-BUTYL)-2,6-DINITROANILINE ON CROP GROWTH-APPLIED PREPLANT INCORPORATED-PLANTED IMMEDIATELY AFTER CHEMICAL TREATMENT

| Crop | Rate of 4-(t-butyl)-N-(sec-butyl)-2,6-dinitroaniline, Lb/A | Crop ht. 29 days after application, % of check |
| --- | --- | --- |
| Melons | ¾ | 118 |
| Melons | 1.5 | 110 |
| Cucumbers | ¾ | 124 |
| Cucumbers | 1.5 | 128 |
| Tomato | ¾ | 137 |
| Tomato | 1.5 | 126 |
| Cotton | ¾ | 118 |
| Cotton | 1.5 | 124 |
| Untreated | 0 | 100 |

Table XVIII

EFFECT OF 4-TERT-BUTYL-N-SEC-BUTYL-2,6-DINITROANILINE ON CROP GROWTH-CHEMICAL APPLIED PREPLANT INCORPORATED-PLANTED THREE WEEKS AFTER TREATMENT

| Crop | Rate of 4-tert-butyl-N-sec-butyl-2,6-dinitroaniline, lb/A | crop ht. 48 days after treatment and 27 days after planting. % of check |
| --- | --- | --- |
| Melons | ¾ | 114 |
| Melons | 1.5 | 114 |
| Cucumbers | ¾ | 129 |
| Cucumbers | 1.5 | 104 |
| Tomato | ¾ | 160 |
| Tomato | 1.5 | 156 |
| Cotton | ¾ | 147 |
| Cotton | 1.5 | 138 |
| Untreated | 0 | 100 |

EVALUATION 13

EFFECT OF 4-TERT-BUTYL-N-SEC-BUTYL-2,6-DINITROANILINE ON GROWTH OF CANTALOUPES AND COTTON USING STERILIZED SOIL TECHNIQUE

The following study employed a soil sterilant to remove any possible competing weed population, in order that any growth stimulant effect would not be attributed merely to removal of weed competition for soil nutrients.

The entire test area was treated with a soil sterilant (methyl bromide) to provide weed free conditions throughout the growing season. Any weeds that emerged were eliminated by careful hand removal. Individual plots were comprised of 2 rows 40 feet long with each test replicated 6 times. Tests were conducted with cantaloupes and cotton as representative test crops. In the case of cantaloupes, seeds were planted on May 27 in sterilized sand loam soil fertilized with ammonia nitrate about 1 inch deep with 6 to 9 seeds per foot. Prior to planting the prepared soil bed for the test plots was treated with test chemical at one pound per acre incorporated to 2 inches with a tilrovator. Crop was harvested in four stages, on August 26, September 2, September 7, and September 13, respectively, and weighed for comparison of total yields.

In the case of cotton the soil bed was prepared for planting as in the case of cantaloupes, test plots were 2 rows 50 feet long replicated 6 times. Test compounds were incorporated to 2 inches as with the cantaloupe plots. Cotton seed was planted on May 28 at 1½ inches at 25 pounds of seed per acre. The cotton lint and seed was harvested on November 26 and weighed for comparison of total yields.

The results are shown below. Both the test plots and the checks were weed free throughout the growing season. The only difference between test plots and checks is the treatment with 4-tert-butyl-N-sec-butyl-2,6-dinitroaniline in the test plots.

Table XIX

CANTALOUPES
Aggregate weight of melon harvest per plot of six replicates

| Date of Harvest | | 1 | 2 | 3 | 4 | 5 | 6 | Avg/Plot | Avg/Acre* |
| --- | --- | --- | --- | --- | --- | --- | --- | --- | --- |
| Aug. 26 | treated (1 lb./A) | 61.3 | 41.7 | 60.7 | 63.9 | 31.5 | 47.1 | 51.0 | 3703 |
| | check | 53.4 | 55.8 | 30.3 | 36.8 | 52.1 | 26.2 | 42.4 | 3078 |
| Sept. 2 | treated (1 lb./A) | 22.6 | 25.0 | 36.5 | 31.5 | 35.8 | 84.2 | 39.3 | 2853 |
| | check | 14.0 | 16.3 | 12.4 | 10.6 | 29.8 | 25.3 | 18.1 | 1314 |
| Sept. 7 | treated (1 lb./A) | 51.2 | 79.9 | 110.5 | 90.7 | 111.8 | 67.0 | 85.2 | 6185 |
| | check | 80.1 | 53.8 | 87.1 | 58.6 | 107.9 | 112.4 | 83.3 | 6048 |
| Sept. 13 | treated (1 lb./A) | 14.8 | 41.3 | 44.5 | 53.1 | 47.8 | 21.7 | 37.2 | 2701 |
| | check | 20.3 | 20.0 | 22.3 | 25.5 | 39.3 | 38.0 | 27.6 | 2004 |

*adjusted for ratio of plot size to 1 acre (1 to 72.6)

Table XX

| | CANTALOUPE HARVEST | |
| --- | --- | --- |
| | TREATED Avg/Acre | CHECK Avg/Acre |
| Aug. 26 | 3703 | 3078 |
| Sept. 2 | 2853 | 1314 |
| Sept. 7 | 6185 | 6048 |
| Sept. 13 | 2701 | 2004 |
| Total Harvest | 15442 lbs. | 12444 lbs. |

Table XXI

| | COTTON Lbs. harvested per plot for six replicates | | | | | | | |
|---|---|---|---|---|---|---|---|---|
| | 1 | 2 | 3 | 4 | 5 | 6 | Avg/Plot | Avg/Acre* |
| Treated (1½ lbs./A) | 10 | 12 | 17 | 20 | 19 | 13 | 15 | 2078 |
| Check | 13 | 13 | 15 | 12 | 14 | 14 | 14 | 1857 |

*adjusted for ratio of plot size to 1 acre (1 to 137.6)

The foregoing results, based on actual field conditions, indicate 4-tert-butyl-N-sec-butyl-2,6-dinitroaniline when applied as a selective preplant incorporated herbicide at a herbicidally effective rate to cantaloupes and cotton results in a substantial increase in the average yield (12% in the case of cotton and 24% in the case of cantaloupes.

The yield stimulant effect indicated by the foregoing test results is in accord with recognized plant growth regulant properties of 4-tert-butyl-N-sec-butyl-2,6-dinitroaniline as demonstrated by its tobacco sucker control effect.

COMPARISON OF 4-(TERT-BUTYL)-N-(SEC-BUTYL)-2,6-DINITROANILINE WITH PRIOR ART COMPOUNDS

EVALUATION 14

4-TERT-BUTYL-N-SEC-BUTYL-2,6-DINITROANILINE ON SOYBEANS

Location — Grenada, Mississippi
Variety — Bragg
Treated — 22 May — Preplant incorporated — 4-tert-butyl-N-sec-butyl-2,6-dinitroaniline
Rate of 4-tert-butyl-N-sec-butyl-2,6-dinitroaniline — 1½ lb/A
Standard — 2½ lb./A of chloramben — Applied preemergence 22 May
Soil — Sandy loam
Plot Size — 0.7 A The 4-tert-butyl-N-sec-butyl-2,6-dinitroaniline plot was observed to be producing plants that were more robust and vigorous than the untreated check or the chloramben plot. Weed control was fine in 4-tert-butyl-N-sec-butyl-2,6-dinitroaniline and chloramben plots but unsatisfactory in the untreated check. Weed competition repressed growth in the untreated plot. Chloramben is a standard weed control treatment and weed control was equal to 4-tert-butyl-N-sec-butyl-2,6-dinitroaniline. No injury was observed from this standard treatment.

There was an obvious increase in plant growth later in the season with the 4-tert-butyl-N-sec-butyl-2,6-dinitroaniline treatment. Stalk diameter was also evaluated. Results are shown in the Table below.

Pods were harvested from the 10 average plants selected from 20 plants harvested at random.

Table XXII

| | SOYBEAN STALK DIAMETER (CM) | |
|---|---|---|
| Sample No. | 4-tert-butyl-N-sec-butyl-2,6-dinitroaniline | Standard |
| 1 | 1.1 | 0.78 |
| 2 | 1.0 | 0.68 |
| 3 | 1.25 | 0.90 |
| 4 | 1.1 | 0.75 |
| 5 | 1.3 | 0.80 |
| 6 | 1.2 | 0.52 |
| 7 | 1.25 | 0.60 |
| 8 | 1.2 | 0.95 |
| 9 | 1.3 | 0.50 |
| 10 | 1.25 | 0.80 |
| 11 | 1.4 | 0.80 |
| 12 | 1.25 | 0.60 |
| Total | 14.60 | 8.68 |
| Average | 1.21 | 0.723 |
| Cm. diameter increase | 0.487 | — |
| % Increase in stem diameter (% of standard) | 67.4 % | 0 % |

Table XXIII

| | SOYBEAN YIELDS | | |
|---|---|---|---|
| Treatment | Yield | Increase in Yield | % Increase in Yield |
| 4-tert-butyl-N-sec-butyl-2,6-dinitroaniline | 6 lb. 8 oz. | 4 lb. 6 oz. | 205.8 % |
| Standard | 2 lbs. 2 oz. | — | — |

EVALUATION 15

4-TERT-BUTYL-N-SEC-BUTYL-2,6-DINITROANILINE — SNAP BEANS

Location — Loveland, Colorado
Treatments established — 15 May
Individual Plots — 20 feet × 50 feet in size
Incorporation Method — Chisel cultivator followed by spike tooth harrow and mulcher — within 45 minutes of application.

Table XXIV

| | SNAP BEAN YIELD | | | | | |
|---|---|---|---|---|---|---|
| | Percent Control | | Snapbean yield/plot (lbs) | | | |
| | Pigweed | Setaria | I* | II* | Total | % of Check |
| 4-tert-butyl-N-sec-butyl-2,6-dinitroaniline at 1 lb/A | 90 | 100 | 15.2 | 13.3 | 28.5 | 125 |
| 4-tert-butyl-N-sec-butyl-2,6-dinitroaniline at 1½ lb/A | 96 | 96 | 15.8 | 13.4 | 29.2 | 128 |
| 4-tert-butyl-N-sec-butyl-2,6-dinitroaniline at 3 lb/A | 98 | 98 | 14.6 | 14.7 | 29.3 | 129 |

Table XXIV-continued

| | SNAP BEAN YIELD | | | | | |
|---|---|---|---|---|---|---|
| | Percent Control | | | Snapbean yield/plot (lbs) | | |
| | Pigweed | Setaria | I* | II* | Total | % of Check |
| trifluralin at ¾ lb/A | 100 | 100 | 11.7 | 11.7 | 23.4 | 103 |

Bean yields taken from 2 rows × 145 feet.
*Sample areas within each individual plot (1 row × 15 feet).

EVALUATION 16

4-TERT-BUTYL-N-SEC-BUTYL-2,6-DINITROANILINE ON COTTON

Test A

Location — Greenville, Mississippi
Rate/A — 3 lbs.
Soil — Medium loam
Planted — 30 April
Treated — 28 April
Variety — DPL Vegetative growth of cotton was enhanced as a result of the 3 lb/A treatment of 4-tert-butyl-N-sec-butyl-2,6-dinitroaniline. Growth was observed to be increased from 10 to 50% when the cotton was 15 inches tall. The increase in growth was not only in height but in lateral growth also.

Test B

Location — Greenville, Mississippi
Variety — DPL
Planted — April 22
Treated — April 20
Rate/A — 2 lb.
Soil — Loam The 4-tert-butyl-N-sec-butyl-2,6-dinitroaniline was compared with the untreated check and with ¾ lb/A of trifluralin. The 4-tert-butyl-N-sec-butyl-2,6-dinitroaniline treatment showed increased vigor and general robustness of the plants. Four independent observers picked the 4-tert-butyl-N-sec-butyl-2,6-dinitroaniline plot as being superior to the untreated check or the trifluralin treatment. The increase in plant growth on the 4-tert-butyl-N-sec-butyl-2,6-dinitroaniline plot was rated 15–20% above the check and the trifluralin treatment.

Test C

Location — Benoit, Mississippi
Planted — May 11
Treated — May 10
Rate/A — 2 lbs.
Soil — Medium Clay Loam
Plot Size — 6 rows × 300

The 4-tert-butyl-N-sec-butyl-2,6-dinitroaniline was compared to an untreated check. Initially lateral root repression was observed on the seedling cotton in the 4-tert-butyl-N-sec-butyl-2,6-dinitroaniline treated area. When the check row plants averaged 36 inches tall the 4-tert-butyl-N-sec-butyl-2,6-dinitroaniline treatment was 48 inches to 54 inches tall. At this time the root development was excellent on the 4-tert-butyl-N-sec-butyl-2,6-dinitroaniline cotton. The increase in root development indicated root stimulation as the concentration of 4-tert-butyl-N-sec-butyl-2,6-dinitroaniline was reduced by microorganisms. (Typical growth regulator response). The 33.3% to 50% increase in plant size of the 4-tert-butyl-N-sec-butyl-2,6-dinitroaniline cotton versus the check was partially due to the weed competition, however, according to expert observers, the weed density could not account for all the difference.

EVALUATION 17

4-TERT-BUTYL-N-SEC-BUTYL-2,6-DINITROANILINE ON POTATOES

The test compound was preplant incorporated at 1½ lbs. per acre in plots 10 feet × 40 feet with potatoes planted in 4 rows in each plot. Weed control was excellent. Yield data is based on three replications for each treatment and controls. The potatoes from all plots were graded into market grade (Number 1 and Grade B) and culls. The increase in market grade potatoes (Grade B) treated with 4-tert-butyl-N-sec-butyl-2,6-dinitroaniline is shown in percent of control and represents a significant increase over that obtained with the standard weed control application of ½ lb. trifluralin plus 2 lbs. EPTC.

Table XXV

4-TERT-BUTYL-N-SEC-BUTYL-2,6-DINITROANILINE ON POTATOES

| Treatment | Rate lb/A ai | Percent of Control Market Grade Potatoes | |
|---|---|---|---|
| | | No. 1 | Grade B |
| 4-tert-butyl-N-sec-butyl-2,6-dinitroaniline | 1½ | 169 | 159 |
| Trifluralin + EPTC | ½ + 2 | 169 | 128 |

EVALUATION 18

COMPARISON OF 4-TERT-BUTYL-N-SEC-BUTYL-2,6-DINITROANILINE AND TRIFLURALIN ROOT PRUNING

In the following test both 4-tert-butyl-N-sec-butyl-2,6-dinitroaniline and trifluralin were applied to cotton in a banded treatment. Subsequently, the root system of the cotton plants in the test plots were uncovered and measurements taken thereof to provide the data for this test.

Table XXVI

| Chemical | Rate lb/A | Expt. No. | Length of Tap Root per plant (mm) | Number of Lateral Roots per Plant | Number of Lateral Roots in the Treated Band |
|---|---|---|---|---|---|
| 4-tert-butyl-N-sec-butyl-2,6-dinitroaniline | 1.0 | I | 165.0 | 29.8 | 11.3 |
| | 1.0 | II | 174.3 | 36.9 | 14.5 |
| | | Ave. | 169.7 | 33.4 | 12.9 |
| 4-tert-butyl-N- | 2.0 | I | 161.3 | 28.1 | 8.8 |

Table XXVI-continued

| Chemical | Rate lb/A | Expt. No. | Length of Tap Root per plant (mm) | Number of Lateral Roots per Plant | Number of Lateral Roots in the Treated Band |
|---|---|---|---|---|---|
| sec-butyl-2,6-dinitroaniline | 2.0 | II | 179.6 | 28.1 | 4.2 |
|  |  | Ave. | 171.0 | 28.1 | 6.5 |
| Trifluralin | 0.5 | I | 155.0 | 22.2 | 3.7 |
|  | 0.5 | II | 186.9 | 26.0 | 0.9 |
|  |  | Ave. | 171.0 | 24.1 | 2.3 |
| Trifluralin | 1.0 | I | 156.3 | 22.7 | 1.0 |
|  | 1.0 | II | 166.8 | 23.2 | 0.4 |
|  |  | Ave. | 161.6 | 23.0 | 0.7 |

The reduction of the number of lateral roots on each cotton plant in the treated band by the trifluralin was quite pronounced.

EVALUATION 19

COMPARATIVE TRIALS IN RICE — 4-TERT-BUTYL-N-SEC-BUTYL-2,6-DINITROANILINE AND TRIFLURALIN

Paddy was rotovated twice and cultipacked prior to planting Nova 66 rice, applying treatments July 3, and flooding. Barnyardgrass was broadcast on the plot area before final fitting. Irrigation and rainfall accumulated July 4 to 16 totaled 11.25 inches. Evaluations were made August 11. 4-tert-butyl-N-sec-butyl-2,6-dinitroaniline selectivity was good; trifluralin injury was 70% at 0.5 lb/A.

Table XXVII

RESPONSE OF FLOODED RICE AND WEEDS TO PREEMERGENCE TREATMENT

| Chemical | Rate lb/A ai | Rice | % Plant Control Broadleaf weeds | Barnyard grass |
|---|---|---|---|---|
| 4-tert-butyl-N-sec-butyl-2,6-dinitroaniline | 0.50 | 16 | 80 | 83 |
| Trifluralin | 0.50 | 70 | 100 | 96 |

EVALUATION 20

COMPARATIVE FIELD TRIALS WITH 4-TERT-BUTYL-N-SEC-BUTYL-2,6-DINITROANILINE AND DINITROANILINE HERBICIDES

Herbicide field screening trials were conducted. Soil type varied from silty loam to silty clay loam. All plots were replicated three times.

Table XXVIII

AVERAGE PERCENT CONTROL ON CROPS AND WEED SPECIES

| Treatment | Rate lb/A | Cucumber | Corn | Soybeans | Ryegrass | Cotton | Tomatoes | Wheat | Barnyardgrass | Pigweed | Morningglory | Coffeeweed | Purslane |
|---|---|---|---|---|---|---|---|---|---|---|---|---|---|
| Preplant incorporated |  |  |  |  |  |  |  |  |  |  |  |  |  |
| 4-tert-butyl-N-sec-butyl-2,6-dinitroaniline | 0.75 | 0 | 3 | 0 | 97 | 0 | 0 | 40 | 73 | 77 | 0 | 0 | 97 |
| 4-tert-butyl-N-sec-butyl-2,6-dinitroaniline | 1.50 | 0 | 33 | 0 | 97 | 7 | 20 | 33 | 77 | 100 | 63 | 0 | 97 |
| 4-tert-butyl-N-sec-butyl-2,6-dinitroaniline | 3.00 | 0 | 50 | 10 | 97 | 0 | 47 | 83 | 97 | 97 | 67 | 0 | 93 |
| Trifluralin | 0.50 | 40 | 10 | 17 | 93 | 33 | 23 | 70 | 93 | 97 | 0 | 0 | 93 |
| Trifluralin | 0.75 | 43 | 33 | 33 | 100 | 0 | 40 | 83 | 93 | 97 | 10 | 7 | 97 |
| Trifluralin | 1.50 | 37 | 37 | 27 | 100 | 30 | 77 | 93 | 97 | 100 | 37 | 17 | 100 |
| Planavin | 0.50 | 27 | 27 | 3 | 57 | 0 | 7 | 60 | 60 | 63 | 63 | 0 | 67 |
| Planavin | 0.75 | 10 | 33 | 10 | 97 | 7 | 10 | 93 | 90 | 97 | 10 | 7 | 97 |
| Planavin | 1.50 | 20 | 17 | 30 | 77 | 13 | 27 | 97 | 93 | 100 | 37 | 27 | 100 |

Treatments were applied and evaluated 34 days later. Rain and irrigation totalled 4.45 inches during this test period.

At 1 lb/A 4-tert-butyl-N-sec-butyl-2,6-dinitroaniline was active against the annual grass species, pigweed and purslane.

Table XXIX

AVERAGE PERCENT CONTROL OF CROPS AND WEED SPECIES

| Treatment | Rate lb/A | Cucumber | Corn | Soybeans | Ryegrass | Cotton | Tomatoes | Wheat | Barnyardgrass | Pigweed | Purslane |
|---|---|---|---|---|---|---|---|---|---|---|---|
| Preplant incorporated |  |  |  |  |  |  |  |  |  |  |  |
| 4-tert-butyl-N-sec-butyl-2,6-dinitroaniline | 1.0 | 0 | 0 | 0 | 87 | 0 | 7 | 47 | 100 | 87 | 93 |
| Trifluralin | 1.0 | 57 | 90 | 0 | 100 | 67 | 73 | 100 | 100 | 93 | 93 |
| Planavin | 1.0 | 7 | 80 | 0 | 100 | 0 | 73 | 100 | 100 | 77 | 66 |

EVALUATION 21

COMPARATIVE TRIALS ON CORN

Pigweed, lambsquarter and barnyardgrass were broadcast seeded prior to the last discing. Agway 800 Hybrid corn was planted and treated August 13. Subsurface moisture was adequate. Plots received a total of 4.6 inches of rain and irrigation before rating on September 19.

At 2 lb/A 4-tert-butyl-N-sec-butyl-2,6-dinitroaniline provided 90% control of pigweed and lambsquarters, and 100% control of barnyardgrass with excellent crop tolerance; trifluralin and nitralin reduced corn height 20% and 10% respectively. A 4-tert-butyl-N-sec-butyl-2,6-dinitroaniline was as active at equal rates of trifluralin or nitralin with significantly greater safety to the corn.

Table XXX

RESPONSE TO LATE-PLANTED CORN AND WEEDS

| Chemical | Rate lb/A ai | Corn | Pigweed | Lambs-quarter | Barnyard-grass |
|---|---|---|---|---|---|
| 4-tert-butyl-N-sec-butyl-2,6-dinitroaniline | 2 | 0 | 90 | 90 | 100 |
| Trifluralin | 2 | 20 | 90 | 85 | 100 |
| Nitralin | 2 | 10 | 90 | 95 | 100 |

EVALUATION 22

CROP SELECTIVITY AND WEED CONTROL OF 4-TERT-BUTYL-N-SEC-BUTYL-2,6-DINITROANILINE AND TRIFLURALIN

The chemical was sprayed on the ground and incorporated. The seeds planted and 4 weeks later the results noted.

| Chemical | Rate, lbs/acre |
|---|---|
| EPTC | 3 |
| 4-tert-butyl-N-sec-butyl-2,6-dinitroaniline | 1 |
| Trifluralin | ¾ |
| Nitralin | 1 |
| 4-tert-butyl-N-sec-butyl-2,6-dinitroaniline | 1 + 2 |

Weed species present were *Amaranthus retroflexus, Chenopodium album, Kochia, Solanum rostratum, Helianthus echinochloa* and *Setaria*.

Incorporation Methods

EPTC, trifluralin and 4-tert-butyl-N-sec-butyl-2,6-dinitroaniline;
Double disced and double harrowed within 1 hour of application;
Incorporation depth approximately 2½ inches.
Other PPI treatments double harrowed only.
Good spray conditions.

Alfalfa showed good tolerance to 4-tert-butyl-N-sec-butyl-2,6-dinitroaniline at the highest rate of 2 lbs/acre. The 1 and ½ lb. per acre rate provided excellent broadleaf and grass control with acceptable control at 1 lb. per acre.

Trifluralin at ¾ lb. per acre provided very acceptable weed control but produced significant alfalfa stand and vigor reduction.

Table XXXI

CROP SELECTIVITY AND WEED CONTROL OF 4-TERT-BUTYL-N-SEC-BUTYL-2,6-DINITROANILINE AND TRIFLURALIN

| Replication Number | Chemical | Rate lb/A ai | Tomato | Soybeans | Cucumber | Lambs-quarters | Pigweed | Grass | Carpet Weed | Purslane |
|---|---|---|---|---|---|---|---|---|---|---|
| 1 | 4-tert-butyl-N-sec-butyl-2,6-dinitroaniline | 1½ | 0 | 0 | 0 | 99 | 99 | 100 | 100 | 100 |
|  | Trifluralin | 1½ | 40 | 0 | 100 | 99 | 100 | 100 | 100 | 100 |
| 2 | 4-tert-butyl-N-sec-butyl-2,6-dinitroaniline | 1½ | 0 | 0 | 25 | 99 | 99 | 100 | 100 | 100 |
|  | Trifluralin | 1½ | 40 | 0 | 100 | 100 | 100 | 100 | 100 | 100 |
| 3 | 4-tert-butyl-N-sec-butyl-2,6-dinitroaniline | 1½ | 0 | 0 | 0 | 95 | 95 | 100 | 100 | 100 |
|  | Trifluralin | 1½ | 0 | 0 | 55 | 99 | 100 | 100 | 100 | 100 |

EVALUATION 23

WEED CONTROL AND SELECTIVITY TO ALFALFA OF 4-TERT-BUTYL-N-SEC-BUTYL-2,6-DINITROANILINE AND TRIFLURALIN

Seedbeds of clay loam were prepared and treatment by the compressed air boom method for weed control in seedling alfalfa were made on May 12 and June 3. Condition of the soil was excellent. Two replications approximately 500 ft$^2$ (vol/plot 43.5 GPA) were prepared, irrigated by furrow corrugates and treated prior to planting to alfalfa. Chemicals employed in these tests and rates of application were as follows:

EVALUATION 24

CROP SELECTIVITY OF 4-TERT-BUTYL-N-SEC-BUTYL-2,6-DINITROANILINE AND TRIFLURALIN

Treatments with 4-tert-butyl-N-sec-butyl-2,6-dinitroaniline were tested in a multi-crop herbicide screening trial. This screening trial was in a sandy soil with 4% organic matter. Five inches of rain fell during the early stages of the trial; there was no irrigation.

Table XXXII

RESPONSE OF CROP SPECIES

| | 4-tert-butyl-N-sec-butyl-2,6-dinitroaniline ppi 1.5 lb/A | | Trifluralin ppi | |
|---|---|---|---|---|
| | % stand reduction | % growth reduction | % stand reduction | % growth reduction |
| Alfalfa | 0 | 0 | 0 | 20 |
| Trefoil | 0 | 0 | 0 | 20 |
| Red clover | 0 | 0 | 0 | 20 |
| White clover | 0 | 0 | 0 | 20 |
| Rape | 0 | 0 | 0 | 20 |
| Spinach | 0 | 0 | 20 | 30 |
| Tomatoes | 0 | 10 | 0 | 30 |
| Rice | 0 | 0 | 50 | 50 |
| Sugar beets | 0 | 0 | 90 | 90 |
| Oats | 10 | 20 | 30 | 70 |
| Rye | 0 | 0 | 30 | 30 |
| Barley | 0 | 0 | 30 | 20 |
| Peas | 0 | 0 | 30 | 30 |
| Field corn | 0 | 0 | 30 | 50 |
| Sunflower | 0 | 0 | 20 | 30 |
| Potatoes | 0 | 0 | 0 | 20 |

EVALUATION 25

POTATO TRIALS WITH 4-TERT-BUTYL-N-SEC-BUTYL-2,6-DINITROANILINE AND TRIFLURALIN FOR WEED CONTROL AND SELECTIVITY

Crops Tested:
Two rows of Irish Cobbler white potatoes, 30 inch spacing, planted on 23 May with the tree planter.

Weed Species Present for Evaluation

Pigweed — Amaranthus retroflexus
Lambsquarter — Chenopodium album
Ragweed — Ambrosia artemisiifolia
Barnyardgrass — Echinochloa crusgalli
Giant foxtail — Setaria faberii Seedbed Preparation Disced three times and cultipacked twice prior to planting. Prior to the last discing 500 lb/acre of 10-20-20 was applied.

Incorporated Treatments .

Applications were made on 23 May with the improved bicycle sprayer, 4 No. 8003 nozzles, 18 inches apart, 18 inches spray height, 20 lb. pressure, 40 gal./acre. Treatments were incorporated with the powered rotovator. Plot size was 6 feet × 10 feet.

Table XXXIII

POTATO TRIALS

| Incorporated No. | Chemical | Rate lb/A ai | Potatoes | Giant Foxtail | Barnyard grass | Lambs-quarter | Pig-weed | Rag-weed |
|---|---|---|---|---|---|---|---|---|
| 1 | 4-tert-butyl-N-sec-butyl-2,6-dinitroaniline | ¾ | 0 | 95 | 95 | 85 | 93 | 0 |
| 2 | Trifluralin | ¾ | 23 | 95 | 95 | 87 | 95 | 0 |

4-tert-butyl-N-sec-butyl-2,6-dinitroaniline was as active as trifluralin on a pound-for-pound basis. However, trifluralin was causing a 23% reduction in potato growth at the ¾ lb/A rate, whereas the 4-tert-butyl-N-sec-butyl-2,6-dinitroaniline appeared quite selective up to as high as 1½ lb/A.

EVALUATION 26

PHOTOLYTIC DEGRADATION OF 4-TERT-BUTYL-N-SEC-BUTYL-2,6-DINITROANILINE AS COMPARED TO TRIFLURALIN

Field observance of the apparent photolytic degradation of trifluralin as compared to the lack of such photolytic degradation on the part of 4-tert-butyl-N-sec-butyl-2,6-dinitroaniline was confirmed by the following test.

A 10,000 ppm solution of both the 4-tert-butyl-N-sec-butyl-2,6-dinitroaniline and the trifluralin in methanol was prepared and applied by spotting to four 10 × 20 cm Chromagram Silica Gel plates. These plates were individually wrapped in a protective plastic film, and then exposed to fluorescent light from four bulbs in a Chromato-Vue viewer for a period of 89 hours. At the end of this exposure period the Chromagram plates were solvent developed with benzene: cyclohexane in a 2:1 volume to volume ratio. Visual examination of the developed plates clearly indicated that the trifluralin had experienced a much greater degree of photolytic degradation than had the 4-tert-butyl-N-sec-butyl-2,6-dinitroaniline, as evidenced by the chromatrographic separation of the photolysis degradation products, clearly visible on the Chromagram plates.

EVALUATION 27

4-TERT-BUTYL-N-SEC-BUTYL-2,6-DINITROANILINE BEAN TRIAL 1.0 lb/A of 4-tert-butyl-N-sec-butyl-2,6-dinitroaniline formulated as a 4 lb/gal. active emulsifiable concentrate was applied prior to planting. The chemical was incorporated by double discing the soil to a depth of 3.5 inches. The standard rate of trifluralin ½ lb/A was applied for comparison.

Location — Patterson, California
Variety — Henderson baby lima beans
Plot Size — 63 feet × 225 feet — 0.325 A
Harvest — 22 September
Volume — 30 gal/A

Table XXXIV

| | YIELD OF BEANS | | |
|---|---|---|---|
| Treatment | Yield per plot | 100 lb bags/A | Yield increase |
| 4-tert-butyl-N-sec-butyl-2,6-dinitroaniline at 1 lb/A | 1,020 lbs | 31.4 | 25.6 % |
| Trifluralin at ½ lb/A | 812 lbs | 25.0 | — |

In order to determine the comparative properties between 4-(t-butyl)-N-(sec-butyl)-2,6-dinitroaniline, one of the novel compounds of this invention, and closely related structural analogs, as taught by the prior art, the comparative tests described below were performed.

EVALUATION 28
WEED CONTROL

Test flats were prepared from soil blended with fertilizer, sand and peat moss and prepared for seeding in replicates of about 10 inches by about 20 inches and about 2 to 3 inches deep. The flats were seeded with the test species in rows, covered with soil and watered till moist to feel. The test chemicals were sprayed on the surface of the flats before seeding, and incorporated into top 1 inch of soil. The results were observed by comparison to controls 4 to 5 weeks after seeding. The percent control in the case of grass weeds and broadleaf weeds is based upon the number and vigor of weeds emerging in the treated flat as compared to the untreated controls.

Table XXXV

| Grass and Broadleaf Weed Species | 4-(t-butyl)-N-(sec-butyl) ½ No. A | 4-(t-butyl)-N-(sec-butyl) 1 No./A | 4-(t-butyl)-N-(n-butyl) ½ No. A | 4-(t-butyl)-N-(n-butyl) 1 No./A |
| --- | --- | --- | --- | --- |
| cheatgrass | 80 | 100 | 30 | 70 |
| annular ryegrass | 95 | 100 | 0 | 50 |
| giant foxtail | 95 | 100 | 50 | 90 |
| crabgrass | 100 | 100 | 75 | 95 |
| barnyard grass | 95 | 100 | 50 | 75 |
| alopecurus | 100 | 100 | 10 | 80 |
| coffeeweed | 30 | 50 | 0 | 0 |
| teaweed | 40 | 60 | 0 | 0 |
| pigweed | 95 | 100 | 0 | 40 |
| Average control | 81 % | 90 % | 25 % | 56 % |

2,6-DINITROANILIEN COMPOUND AND RATE OF APPLICATION

The foregoing tests unequivocally establish a clear and unexpected superiority of 4-(t-butyl)-N-(sec-butyl)-2,6-dinitroaniline for use as a broad spectrum herbicide when compared to the known prior art compounds as represented by the closest structural analog 4-(t-butyl)-N-(n-butyl)-2,6-dinitroaniline.

EVALUATION 29
DODDER CONTROL

Test flats were prepared from soil blended with fertilizer, sand and peat moss and prepared for seeding in replicates of about 10 inches by about 20 inches and about 2 to 3 inches deep. The flats were seeded with the test species in rows, covered with soil and watered till most to feel. For preplant incorporated tests the test chemical was sprayed on the surface of the flats before seeding, and incorporated into top 1 inch of soil. For preemergence tests the test chemical was sprayed on the surface of the flats within a few hours after seeding. The results were observed by comparison to controls 4 to 5 weeks after seeding. The percent control is based upon the number and vigor of weeds emerging in the treated flat as compared to the untreated controls.

Table XXXVI

| (No./A) Rate of Application | % Dodder Control with 2,6-dinitroanilines | | | | | |
| --- | --- | --- | --- | --- | --- | --- |
| | 4-(t-butyl)-N-(sec-butyl) | | 4-(t-butyl)-N-(n-butyl) | | 4-(i-propyl)-N-(sec-butyl) | |
| | PPI | PE | PPI | PE | PPI | PE |
| ½ | 0 | 0 | 0 | 0 | 0 | 0 |
| ¾ | 60 | 20 | 0 | 0 | 0 | 0 |
| 1 | 85 | 50 | 0 | 0 | 30 | 0 |
| 2 | — | 90 | 0 | 0 | — | 60 |

As previously demonstrated, in this application alfalfa has an excellent tolerance to 4-(t-butyl)-N-(sec-butyl)-2,6-dinitroaniline at levels sufficient to give better than 85% dodder control.

The foregoing tests unequivocally establish the surprising and unexpected selective herbicidal effectiveness of the use of 4-(t-butyl)-N-(sec-butyl)-2,6-dinitroaniline, as compared to prior art compounds, against a difficult to control weed species — dodder — a problem weed in the production of alfalfa.

EVALUATION 30
CRABGRASS CONTROL

Preemergence treatments of 4-(tert-butyl)-N-(n-butyl)-2,6-dinitroaniline and 4-(tert-butyl)-N-(sec-butyl)-2,6-dinitroaniline were made in the following manner. Four inch pots were filled with unsterilized soil, seeded with large crabgrass, *Digitaria Sanguinalis*, covered with one-half inch of sand, and then sprayed with treatments of the compounds at 0.5, 1.0, 2.0, 4.0, and 8.0 lbs. per acre in 100 gallons per acre. There were five (5) replications for each treatment.

Incorporation treatments with the same two compounds were made in the following manner. Unsterilized soil sufficient to fill five, 4-inch pots were placed on a black plastic sheet sprayed with 10 ml. of the appropriate solution and mixed by the folding technique. The treated soil was then placed in pots, packed firmly, seeded with large crabgrass, and covered with one-half inch of sand. The rates per acre were the same as the preemergence applications.

All treatments were made on November 11 and evaluated on December 18. The following tables are the rate response tables for each method of application.

Table XXXVII

| PREEMERGENCE CONTROL | | | | | |
| --- | --- | --- | --- | --- | --- |
| | Lbs. Per Acre | | | | |
| | ½ No. | 1 No. | 2 No. | 4 No. | 8 No. |
| | | | % Control | | |
| 4-(t-butyl-N-(sec-butyl)-2,6-dinitroaniline | 55 % | 75 % | 87 % | 98 % | 100 % |
| 4-(t-butyl)-N-(n-butyl)-2,6-dinitroaniline | 38 % | 48 % | 73 % | 87 % | 90 % |

Table XXXVIII

POSTEMERGENCE CONTROL

| | ½ No. | 1 No. | Lbs. Per Acre 2 No. | 4 No. | 8 No. |
|---|---|---|---|---|---|
| | | | % Control | | |
| 4-(t-butyl)-N-(sec-butyl)-2,6-dinitroaniline | 45 % | 82 % | 81 % | 100 % | 100 % |
| 4-(t-butyl)-N-(n-butyl)-2,6-dinitroaniline | 0 % | 0 % | 8 % | 56 % | 70 % |

As a preemergence application, the N-(n-butyl) compound is less active on large crabgrass, *Digitaria Sanguinalis*, than the N-(sec-butyl) compound.

At the 50% control level, .4375 lbs. per acre of the N-(sec-butyl) compound are required whereas 1.00 lb. per acre of the N-(n-butyl) compound is required.

When the N-(n-butyl) compound is incorporated into a 4 inch depth, the activity decreases.

At the 50% control level 0.625 lbs./acre are required for the N-(sec-butyl) compound whereas 3.75 lbs. are required for the N-(n-butyl) compound.

The above tests clearly show the surprising and unexpected superiority of the 4-(t-butyl)-N-(sec-butyl)-2,6-dinitroaniline of this invention over the prior art N-(n-butyl) analog.

EVALUATION 31

PERSISTENCE IN CRABGRASS CONTROL

Unsterilized soil was placed in market packs (containers similar to standard flats), seeded with smooth crabgrass, *Digitaria Ischaeum*, and covered with one-half inch of sand.

Applications, three samples each, of 4-(t-butyl)-N-(sec-butyl)-2,6-dinitroaniline at 2 and 4 lbs/acre and 4-(t-butyl)-N-(n-butyl)-2,6-dinitroaniline at 4, 8, 12 and 16 lbs/acre were applied on December 12.

The market packs were reseeded 30 and 75 days later. One week prior to each reseeding the market packs were evaluated.

Reseeding was accomplished by drying out the market packs, removing the sand, seeding and replacing the original sand.

The trials were also run with sterilized soil, as both a preemergence treatment and sprayed directly on the soil.

The following tables are a summary of the results.

COMPOUND A — 4-(t-butyl)-N-(sec-butyl)-2,6-dinitroaniline

COMPOUND B — 4-(t-butyl)-N-(n-butyl)-2,6-dinitroaniline.

Table XXXIX

CONTROL OF SMOOTH CRABGRASS PREEMERGENCE ON STERILIZED SOIL

| Treatment | 0 days | | 30 days | | 70 days | |
|---|---|---|---|---|---|---|
| lbs./acre | A | B | A | B | A | B |
| 2 | 100 % | — | 73 % | — | 20 % | — |
| 4 | 100 % | 99 % | 98 % | 63 % | 82 % | 27 % |
| 8 | — | 100 % | — | 85 % | — | 85 % |
| 12 | — | 100 % | — | 88 % | — | 96 % |
| 16 | — | 100 % | — | 97 % | — | 97 % |

Table XL

CONTROL OF SMOOTH CRABGRASS INCORPORATED IN STERILIZED SOIL

| Treatment | 0 days | | 30 days | | 70 days | |
|---|---|---|---|---|---|---|
| lbs./acre | A | B | A | B | A | B |
| 2 | 100 % | — | 82 % | — | 45 % | — |
| 4 | 100 % | 100 % | 92 % | 63 % | 78 % | 7 % |
| 8 | — | 100 % | — | 85 % | — | 82 % |
| 12 | — | 100 % | — | 85 % | — | 95 % |
| 16 | — | 100 % | — | 95 % | — | 97 % |

Table XLI

CONTROL OF SMOOTH CRABGRASS PREEMERGENCE IN UNSTERILIZED SOIL

| Treatment | 0 days | | 30 days | | 70 days | |
|---|---|---|---|---|---|---|
| lbs./acre | A | B | A | B | A | B |
| 2 | 100 % | — | 10 % | — | 0 % | — |
| 4 | 98 % | 100 % | 95 % | 65 % | 12 % | 10 % |
| 8 | — | 98 % | — | 87 % | — | 85 % |
| 12 | — | 100 % | — | 85 % | — | 95 % |
| 16 | — | 100 % | — | 95 % | — | 98 % |

In order to obtain short term persistence (30 to 45 days) a rate of 4 lbs/acre of 4-(t-butyl)-N-(sec-butyl) is required. To achieve similar control with the N-(n-butyl) compound a rate of 8 lbs/acre is required. However, at this rate, the persistence of the N-(n-butyl) compound is of longer duration than the corresponding active rate of the N-(sec-butyl) compound of this invention at 4 lbs/acre. Thus in addition to a higher rate of the N-(n-butyl) compound required initially, the treatment will remain in the soil for an extended period of time and may prove to be injurious to succeeding crops.

The above tests clearly show the surprising and unexpected superiority of the 4-(t-butyl)-N-(sec-butyl)-2,6-dinitroaniline, of this invention over the prior art N-(n-butyl) analog of the prior art.

EVALUATION 32

FISH CONTROL

Fifteen mg. samples of the 4-(t-butyl)-N-(sec-butyl)-2,6-dinitroaniline compound and the N-(n-butyl) compound were dissolved in 5 ml. of acetone and added to three (3) liters of water. Air was bubbled into each jar to allow for a constant mixing of the compounds and provide for sufficient oxygen. Five 2 to 2½ inch size goldfish were introduced into three jars, two into two jars and one into another jar, containing the treated water for each compound. Two control jars containing three goldfish were also introduced into two other jars containing a 5 ml. acetone blank. The duration of the test was two weeks and the fish were fed a daily basic diet-goldfish food Tetra Fin. Daily observations were made as to the condition of the fish as well as the mortality. The test was started on January 2.

After one week, 2 of the 5 goldfish had died in the N-(sec-butyl) compound of this invention, whereas no fish had died in the N-(n-butyl) compound of the prior art.

After two weeks no additional goldfish were lost with either treatment.

The above tests clearly show the surprising and unexpected property, of controlling fish, possessed by the 4-(t-butyl)-N-(sec-butyl)-2,6-dinitroaniline of this invention. This property is clearly not possessed by the N-(n-butyl) analog of the prior art.

I claim:
1. 4-tert-butyl-N-sec-butyl-2,6-dinitroaniline.
2. D-4-tert-butyl-N-sec-butyl-2,6-dinitroaniline.
3. L-4-tert-butyl-N-sec-butyl-2,6-dinitroaniline.

* * * * *